US011299715B2

(12) United States Patent
Pechan et al.

(10) Patent No.: US 11,299,715 B2
(45) Date of Patent: Apr. 12, 2022

(54) USE OF INOS INHIBITORS TO INCREASE VIRAL YIELD IN CULTURE

(71) Applicant: Genzyme Corporation, Cambridge, MA (US)

(72) Inventors: Peter Pechan, Cambridge, MA (US); Jeffery Ardinger, Canbridge, MA (US); Abraham Scaria, Cambridge, MA (US); Samuel Wadsworth, Cambridge, MA (US)

(73) Assignee: Genzyme Corporation, Cambridge (GB)

( * ) Notice: Subject to any disclaimer, the term of this patent is extended or adjusted under 35 U.S.C. 154(b) by 0 days.

(21) Appl. No.: 14/758,785

(22) PCT Filed: Jan. 7, 2014

(86) PCT No.: PCT/US2014/010553
§ 371 (c)(1),
(2) Date: Jun. 30, 2015

(87) PCT Pub. No.: WO2014/110053
PCT Pub. Date: Jul. 17, 2014

(65) Prior Publication Data
US 2015/0353899 A1 Dec. 10, 2015

Related U.S. Application Data

(60) Provisional application No. 61/750,175, filed on Jan. 8, 2013.

(51) Int. Cl.
*C12N 7/00* (2006.01)

(52) U.S. Cl.
CPC ...... *C12N 7/00* (2013.01); *C12N 2710/16643* (2013.01); *C12N 2710/16651* (2013.01)

(58) Field of Classification Search
None
See application file for complete search history.

(56) References Cited

U.S. PATENT DOCUMENTS

| | | | | |
|---|---|---|---|---|
| 6,783,972 | B1 * | 8/2004 | Byrne | C12N 7/00 435/235.1 |
| 6,833,271 | B2 | 12/2004 | Bertheussen | |
| 7,091,029 | B2 | 8/2006 | Hwang | |
| 7,223,411 | B1 | 5/2007 | Knipe et al. | |
| 7,262,033 | B1 | 8/2007 | Coffin et al. | |
| 2002/0031825 | A1 | 3/2002 | Bertheussen | |

FOREIGN PATENT DOCUMENTS

| | | | |
|---|---|---|---|
| JP | 4044131 | B2 | 2/2008 |
| RU | 2012335 | C1 | 5/1994 |
| WO | WO 2004/027048 | | 4/2004 |

OTHER PUBLICATIONS

Chen et al., Antiviral Chemistry & Chemotherapy, 2009, 20: 19-36.*
Sigma data sheet, 2017.*
Zhang et al., Antiviral Res., 1999, 43: 23-35.*
Schols et al., Proc. Natl. Acad. Sci. U.S.A., 1989, 86: 3322-3326.*
Foster et al., J. Virol. Methods, 1998. 75:151-160.*
Garcia-Vellalon et al., Antiviral Chemistry & Chemotherapy, 1992, 3: 9-14.*
Leary et al., J. Gen. Virol., 1985, 66: 1123-1129.*
Liuzzi et al., Nature, 1994, 372: 695-698.*
Chen et al., "Inhibition of Cytokine-Induced Jak-Stat Signalling Pathways by an Endonuclease Inhibitor Aurintricarboxylic Acid", British Journal of Pharmacology 137:1011-1020 (2002).
Conway et al., "High-Titer Recombinant Adeno-Associated Virus Production Utilizing a Recombinant Herpes Simplex Virus Type I Vector Expressing AAV-2 REP and CAP", Gene Therapy, 6:986-993 (1999).
Dorokhov et al., "Stimulation by Aurintricarboxylic Acid of Tobacco Mosaic Virus-Specific RNA Synthesis and Production of Informosome-Like Infection-Specific Ribonucleoprotein", Virology135(2):395-405 (1984).
Dorokhov et al., "Effect of Aurintricarboxylic-Acid of Tobacco Mosaic Virus Reproduction", Database Biosis [online] Biosciences Information Service, Philadelphia, PA, US, (1981).
Dugo et al., "Effects of GW274150, a Novel and Selective Inhibitor of Inos Activity, in Acute Lung Inflammation", British Journal of Pharmacology, 141:979-987 (2004).
Erlandsson et al., "Herpes Simplex Virus Type 1 Infection and Glucocorticoid Treatment Regulate Viral Yield, Glucocorticoid Receptor and NF-KB Levels", Journal of Endocrinology, 175:165-176 (2002).
Garcia-Villalon et al., Anionic Compounds as Inhibitors of African Swine Fever Virus Replication in Vero Cell, Database Biosis [online] Biosciences Information Service, Philadelphia, PA, US, (1992).
Gil-Fernandez et al., "Aurintricarboxylic Acid: an Inhibitor of Herpes Simplex Types I and II, Vaccinia and African Swine Fever Viruses Replication in Vero Cells", Antiviral Research, Elsevier BV, NL, vol. 15, p. 75 (1991).

(Continued)

*Primary Examiner* — Ileana Popa
(74) *Attorney, Agent, or Firm* — Morrison & Foerster LLP

(57) ABSTRACT

The use of iNOS inhibitors, including aurintricarboxylic acid, dexamethasone and valproic acid, to increase the yield of a variety of viruses in culture, including recombinant herpesviruses is described.

9 Claims, 11 Drawing Sheets

(56) References Cited

OTHER PUBLICATIONS

Hardwicke et al., "Differential Effects of Nerve Growth Factor and Dexamethasone on Herpes Simplex Virus Type 1 Oril- and Oris-Dependent DNA Replication in PC12 Cells", Journal of Virology, 71(5):3580-3587 (1997).
He et al., "Potent and Selective Inhibition of Sars Coronavirus Replication by Aurintricarboxylic Acid", Biochemical and Biophysical Research Communications, 320:1199-1203 (2004).
Karupiah et al., "Inhibition of Viral Replication by Interferon-γ-Induced Nitric Oxide Synthase", Science, 261:1445-1448 (1993).
McFarlane et al., "Hexamethylene Bisacetamide Stimulates Herpes Simplex Virus Immediate Early Gene Expression in the Absence of Trans-induction By VMW65", Journal of General Virology, 73:285-292 (1992).
Motamedifar et al., "Effects of Sodium Valproate on the Replication of Herpes Simplex Virus Type 1: An in Vitro Study", Iran J. Med. Sci., 31(1):28-32 (2006).
Muscara et al., "Nitric Oxide. V. Therapeutic Potential of Nitric Oxide Donors and Inhibitors", American Physiological Society, Nitric Oxide Donors and Inhibitors, G1314-G1316 (2009).
Myskiw et al., "Aurintricarboxylic Acid Inhibits the Early Stage of Vaccinia Virus Replication By Targeting Both Cellular and Viral Factors", Journal of Virology, 81(6):3027-3032 (2007).
Nathan, "Nitric Oxide as a Secretory Product of Mammalian Cells", The FASEB Journal, 6:3051-3064 (1992).
Neyts et al., Polyhydroxycarboxylates as Selective Inhibitors of Cytomegalovirus and Herpes Simplez Virus Replication:, Database Biosis [online] Biosciences Information Service, Philadelphia, PA, US, (1992).
Otsuki et al., "Histone Deacetylase Inhibitors Augment Antitumor Efficacy of Herpes-Based Oncolytic Viruses", The American Society of Gene Therapy, 16(9): 1546-1555 (2008).
Ozuer et al., "Evaluation of Infection Parameters in the Production of Replication-Defective HSV-1 Viral Vectors", Biotechnol. Prog. 18:476-482 (2002).
Pechan et al., "Aurintricarboxylic Acid Increases Yield of HSV-1 Vectors", Molecular Therapy—Methods and Clinical Development, 1(6):1-5 (2014).
Southan et al., "Selective Pharmacological Inhibition of Distinct Nitric Oxide Synthase Isoforms", Biochemical Pharmacology, 51:383-394 (1996).
Walker et al., "Mechanisms of Suppression of Inducible Nitric-Oxide Synthase (Inos) Expression in Interferon (Ifn)-γ-Stimulated Raw 264.7 Cells By Dexamethasone", The Journal of Biological Chemistry, 272(26): 16679-16687 (1997).
Wechuck et al., "Effect of Protease Inhibitors on Yield of HSV-1-Based Viral Vectors". Biotechnol. Prog., 16:493-496 (2000).
Rice, et al., "Herpes Simplex Virus Alpha Protein ICP27 Possesses Separable Positive and Negative Regulatory Activities," Journal of Virology, 63(8):3399-3407 (1989).
Kodukula, P. et al. (1999). "Macrophage Control of Herpes Simplex Virus Type 1 Replication in the Peripheral Nervous System," *The Journal of Immunology* 162:2895-2905.
Kunz D et al. (Dec. 1, 1994). "Dexamethasone Differentially Affects Interleukin 1β- and Cyclic AMP-Induced Nitric Oxide Synthase mRNA Expression in Renal Mesangial Cells," *Journal of Biochem* 304(Pt 2):337-340.

* cited by examiner

| HSV-1 vector /cells | Control: - ATA [DRP/ml] | +ATA [DRP/ml] | Ratio |
|---|---|---|---|
| d27-GFP/V27 cells | $(5.4 \pm 2.7) \times 10^7$ | **$(3.3 \pm 1.2) \times 10^8$ | 6.1 x |
| wtHSV-1 McIntyre/293 cells | $(1.1 \pm 0.5) \times 10^8$ | ***$(1.0 \pm 0.3) \times 10^9$ | 9.1 x |

USE OF INOS INHIBITORS TO INCREASE VIRAL YIELD IN CULTURE

This application is a § 371 filing of PCT/US2014/010553, filed Jan. 7, 2014, and claims the benefit of U.S. provisional application 61/750,175 filed Jan. 8, 2013, from which applications priority is claimed pursuant to 35 U.S.C. §§ 119/120, and which applications are incorporated herein by reference in their entireties.

TECHNICAL FIELD

The present invention relates generally to methods for producing viruses and recombinant virions in culture. In particular, the invention pertains to the use of the iNOS inhibitors, such as aurintricarboxylic acid, dexamethasone and valproic acid to increase the yield of a variety of viruses in culture, including recombinant herpesviruses which can in turn be used as helpers for the production of recombinant adeno-associated virus virions.

BACKGROUND

Herpesviruses are highly disseminated in nature and found in most animal species. At least 100 herpesviruses have been characterized, including several from humans, such as herpes simplex virus-1 (HSV-1) and herpes simplex virus-2 (HSV-2), varicella zoster virus (VZV), Epstein-Barr virus (EBV), cytomegalovirus (CMV) and other human herpesviruses such as HHV6 and HHV7. These viruses are responsible for a variety of human diseases, such as skin infections, genital herpes, viral encephalitis, and the like.

HSV-1 infection activates the host defense and innate immune system by inducing intracellular signaling pathways that lead to the expression of proteins with proinflammatory and microbicidal activities, including cytokines and interferons (INF) (Sainz and Halford, *J. Virol.* (2002) 76:11541-11550; Haller et al., *Virology* (2006) 344:119-130; Paludan et al., *Nat. Rev. Immunol.* (2011) 11:143-154). INF signaling is one of the most important cellular defense mechanism for viral clearance (Brandner & Mueller, *Hoppe-Seyler's Zeitschriftfür physiologische Chemie* (1973) 354: 1176; De Vries et al., *Gene Ther.* (2008) 15:545-552).

Investigators have reported antiviral activity of nitric oxide (NO) against several viruses such as vaccinia virus, vesicular stomatitis virus, and Japanese encephalitis virus, among others (Bi et al., *J. Virol.* (1995) 69:6466-6472; Harris et al., *J. Virol.* (1995) 69:910-915; Lin et al., *J. Virol.* (1997) 71:5227-5235; Pertile et al., *Avian Dis.* (1996) 40:342-348. NO is a free radical gaseous molecule and is a mediator of host defense (Croen K. D., *J. Clin. Invest.* (1993) 91:2446-2452; Karupiah et al., *Science* (1993) 261: 1445-1448; Rolph et al., *Virol.* (1996) 217:470-477; Amaro et al., *J. Med. Virol.* (1997) 51:326-331; Lane et al., *J. Virol.* (1997) 71:2202-2210. HSV-1 is known both to induce and evade host antiviral responses (Mossman et al., *J. Virol.* (2001) 75:750-758). HSV infection is capable of inducing expression of inducible nitric oxide synthase (iNOS), a gene encoding an inducible isoform of NOS that produces large amounts of NO.

Herpesviruses and recombinant proteins therefrom have been used in the manufacture of a number of vaccines. Besides adenoviruses, herpesviruses have been shown to provide complete helper virus functions for the production of recombinant adeno-associated virus virions (Buller, R. M. L., *J. Virol.* (1981) 40:241-247; Mishra et al., *Virology* (1990) 179:632-639). The minimal set of HSV-lgenes required for AAV replication and packaging has been identified as the early genes UL5, UL8, UL52 andUL29 (Weindler et al., *J. Virol.* (1991) 65:2476-2483). These genes encode components of the HSV-lcore replication machinery—the helicase, primase and primase accessory proteins ($U_L5$, $U_L8$ and $U_L52$) and the single-stranded DNA binding protein ($U_L29$).

Recombinant AAV (rAAV) vectors have been successfully used to achieve long-term, high level transduction in vivo. Despite the above advances, production of large quantities of clinical grade high-titer rAAV virions for gene therapy continues to be challenging due to limitations in scalability of the cotransfection protocol. The process requires the efficient cellular delivery of three components: (1) a vector including the gene of interest flanked by AAV inverted terminal repeats (ITRs); (2) a vector including the AAV rep and cap genes; and (3) genes provided using a helper virus, such as adenovirus or herpes simplex virus or using virus-free helper plasmids (see, Muzyczka, N., *Curr. Top. Microbiol. Immunol.* (1992) 158:97-129). Thus, in rHSV-based rAAV manufacturing protocols, the yield of rAAV is limited by the maximal titer of helper rHSV vectors.

A replication-deficient HSV-1 vector, termed d27.1-rc, expresses AAV-2 rep and cap genes (Conway et al., *Gene Ther.* (1999) 6:986-993) and it has been engineered from original d27-1 virus (Rice at al., J. Virol. 1989 vol. 63 (8) pp. 3399-407), that does not produce ICP27, a protein required for HSV-1replication. Although this vector is replication-defective, it does express the HSV-1 early genes required for rAAV replication and packaging (Conway et al., *Gene Ther.* (1999) 6:986-993).

Typically, one vector bearing the rAAV template and the other vector expressing the AAV rep and cap regions are co-infected into 293 cells in order to produce rAAV virions. Both HSV-1 vectors are replication-deficient and can therefore only be propagated in an ICP27-complementing cell line, V27 (Rice at al., J. Virol. 1989 vol. 63 (8) pp. 3399-407). In HSV-based AAV production protocol, 293 cells need to be infected with HSV-1 at a higher multiplicity of infection (MOI) of 12. This represents a limitation, because yields of d27-1-derived vectors in V27 cells are typically around $1\times10^7$ plaque forming units (PFU)/ml.

Several methods and reagents have been investigated in order to further increase HSV-1 titers (see, e.g., Wechuck et al., *Biotechnol. Prog.* (2000) 16:493-496; Ozuer et al., *Biotechnol. Prog.* (2002) 18:476-482; Erlandsson et al., *J. Endocrinol.,* (2002) 175:165-176; Otsuki et al., *Mol. Ther.* (2008) 16:1546-1555). Both dexamethasone and valproic acid inhibited the host defense mechanism represented by several interferon (IFN)-responsive antiviral genes, augmented the transcriptional level of viral genes, and thus improved viral propagation and yield of HSV-1 (Erlandsson et al., *J. Endocrinol.* (2002) 175:165-176; Otsuki et al., *Mol. Ther.* (2008) 16:1546-1555).

Despite the above knowledge, more methods to inhibit host defense in order to improve viral production in culture are needed. As explained above, investigators have reported antiviral activity of nitric oxide (NO) against several viruses such as vaccinia virus, vesicular stomatitis virus, and Japanese encephalitis virus, among others (Bi et al., *J. Virol.* (1995) 69:6466-6472; Harris et al., *J. Virol.* (1995) 69:910-915; Lin et al., *J. Virol.* (1997) 71:5227-5235; Pertile et al., *Avian Dis.* (1996) 40:342-348. NO is a free radical gaseous molecule and is a mediator of host defense (Croen K. D., *J. Clin. Invest.* (1993) 91:2446-2452; Karupiah et al., *Science* (1993) 261:1445-1448; Rolph et al., *Virol.* (1996) 217:470-477; Amaro et al., *J. Med. Virol.* (1997) 51:326-331; Lane et al., *J. Virol.* (1997) 71:2202-2210). As described above, HSV infection can induce expression of iNOS, a gene encoding an inducible isoform of NOS that produces large amounts of NO.

The presence of the iNOS inhibitor N-methyl-L-arginine (L-NMA) reversed the inhibition of viral replication for all three of these viruses (Karupiah et al., *Science* (1993) 261:1445-1448). For a review of iNOS inhibitors, see, Southan et al., *Biochem. Pharmacol.* (1996) 51:383-394. Another compound, aurintricarboxylic acid (ATA), has been shown to protect macrophages from cell death induced by bacterial lipopolysaccharide by downregulation of iNOS expression and thus decreasing the NO production (Chen et al., *British Journal of Pharmacology* (2002) vol. 137 (7) pp. 1011-20). ATA is a heterogeneous mixture of polymers accredited with an increasing number of biological activities, such as interaction with a number of enzymes including DNA polymerases, RNA polymerases, reverse transcriptase (RNA-dependent DNA polymerase), aminoacyl-tRNA-synthetase, ribonucleotide reductase, ribonucleases nuclease, protein synthesis inhibition, prevention of apoptosis and blocking DNA fragmentation in oligodendrocytes induced by oxidative stress (Tscherne and Pestka, *Antimicrob. Agents Chemother.* (1975) 8:479-487; Mikelens et al., *Biochemical Pharmacology* (1976) 25:821-827; Vollgraf et al., *J. Neurochem.* (1999) 73:2501-2509).

Aurintricarboxylic acid (ATA) has been also reported to prevent IFN-mediated transcriptional activation (Tsi et al., *Mol. Pharmacol.* (2002)101:90-101; Chen et al., *British J. Pharmacol.* (2002) 137:1011-1020). ATA is known as an activator of the Raf/MEK/MAPK pathway, IGF-1 receptor and protein kinase C signaling (Beery et al., *Endocrinology* (2001) 142:3098-3107; Chen et al., *J. Biol. Chem.* (2001) 276:46722-46728). Antiviral antimicrobial and antiproliferative actions of cytokines such as interferons may be due to their ability to induce the expression of iNOS, a gene encoding an isoform of nitric oxide synthase (NOS) that produces large amounts of the radical gas, NO, from a guanidino nitrogen of L-arginine (Nathan, C., *FASAB J.* (1992) 6:3051; Werner-Felmayer et al., *J. Exp. Med.* (1990) 172:1599). It has been shown that treatment of macrophages with IFN-γ severely restricts replication of ectromelia virus (EV), vaccinia virus (VV) and HSV-1.

On one hand, ATA is also known as an antiviral agent against several viruses including HIV, herpesvirus HHV-7, SARS-CoV and others (Cushman et al., *J. Med. Chem.* (1991) 34:329-3371991; Zhang et al., *Antiviral Res.* (1999) 43:23-35; Yap et al., *Computational Biol. and Chem.* (2005) 29:212-219; De Clercq, *Advents, Advances, and Adventures Med. Res. Rev.* (2011) 31:118-160). ATA, however, did not block the replication of adenovirus type 5 (Ad5) in HEK-293 cells (He, *Biochem. Biophys. Res. Comm.* (2004) 320: 1199-1203). Moreover, ATA has been reported to unexpectedly increase titer of a control adenovirus vector in 293 cells while at the same time having antiviral effects on vaccinia virus (Myskiw et al., *J. Virol.* (2007) 81:3027-3032).

SUMMARY OF THE INVENTION

The present invention thus overcomes deficiencies in the prior art by addressing problems that limit viral production, such as low production of rHSV, which hampers efforts to produce sufficient quantities of rHSV for a variety of purposes, including for vaccine production, as well as for rAAV virion production in quantities necessary for efficient gene therapy procedures. Using the methods described herein, higher titers of a variety of viruses can be obtained, such as at least an order of magnitude greater than traditional methods.

In particular, the inventors herein have discovered that aurintricarboxylic acid (ATA) inhibits iNOS and increases HSV production. As shown in the examples herein, micromolar concentrations of ATA in the presence of fetal bovine serum (FBS) increased both HSV-1/d27-1 vector yield in V27 cells and wild-type (wt) HSV-1 virus in Vero, V27 and 293 cells. Other iNOS inhibitors, including dexamethasone and valproic acid, also increased HSV-1 titers in culture. HSV-induced iNOS expression was shown to be reduced in HSV+ATA samples as analyzed by SABiosciences Microarray. Similarly, Affymetrix human genome array analysis confirmed that expression of HSV-up-regulated all three nitric oxide synthase genes (nNOS, iNOS and eNOS) were down-regulated n HSV+ATA samples. Affymetrix Gene Array also detected that genes involved in inflammatory IgE and IFN signaling, and general immune responses were upregulated by HSV-1 and suppressed after the addition of ATA. On the other hand, genes primarily involved in cell cycle G1/S, signal transduction in WNT development were significantly down-regulated by HSV and upregulated after addition of ATA.

These results are significant because of the demand for higher HSV-1 titers for rAAV virion production, as well as for prophylactic, therapeutic and diagnostic purposes.

Accordingly, in one embodiment the invention is directed to a method for producing a virus comprising culturing the virus in a cell culture that comprises aurintricarboxylic acid. In certain embodiments, the virus is a herpesvirus, such as HSV-1.

In additional embodiments, the herpesvirus is a wild type HSV-1 or a recombinant HSV-1 vector, such as an HSV-1 d27.1 vector.

In further embodiments, the virus is cultured in 293, HeLa or Vero cells, such as V27 cells.

In yet additional embodiments, the invention is directed to a method for culturing an HSV-1 d27.1 vector comprising:

(a) infecting V27 cells with an HSV-1 d27.1 vector; and (b) culturing the infected V27 cells in a cell culture comprising aurintricarboxylic acid, valproic acid or dexamethasone.

In certain embodiments, the cell culture further comprises serum, such as fetal bovine serum.

In further embodiments, the invention is directed to a cell culture comprising aurintricarboxylic acid and 293, HeLa or Vero cells, such as V27 cells.

These and other embodiments of the subject invention will readily occur to those of skill in the art in view of the disclosure herein.

BRIEF DESCRIPTION OF THE FIGURES

FIG. 2B shows viral titers expressed as DNase resistant particles (DRP/ml) at various ATA concentrations in six well plates (FIG. 2B) and T150 flasks (FIG. 2C).

DETAILED DESCRIPTION OF THE INVENTION

Figure 1:
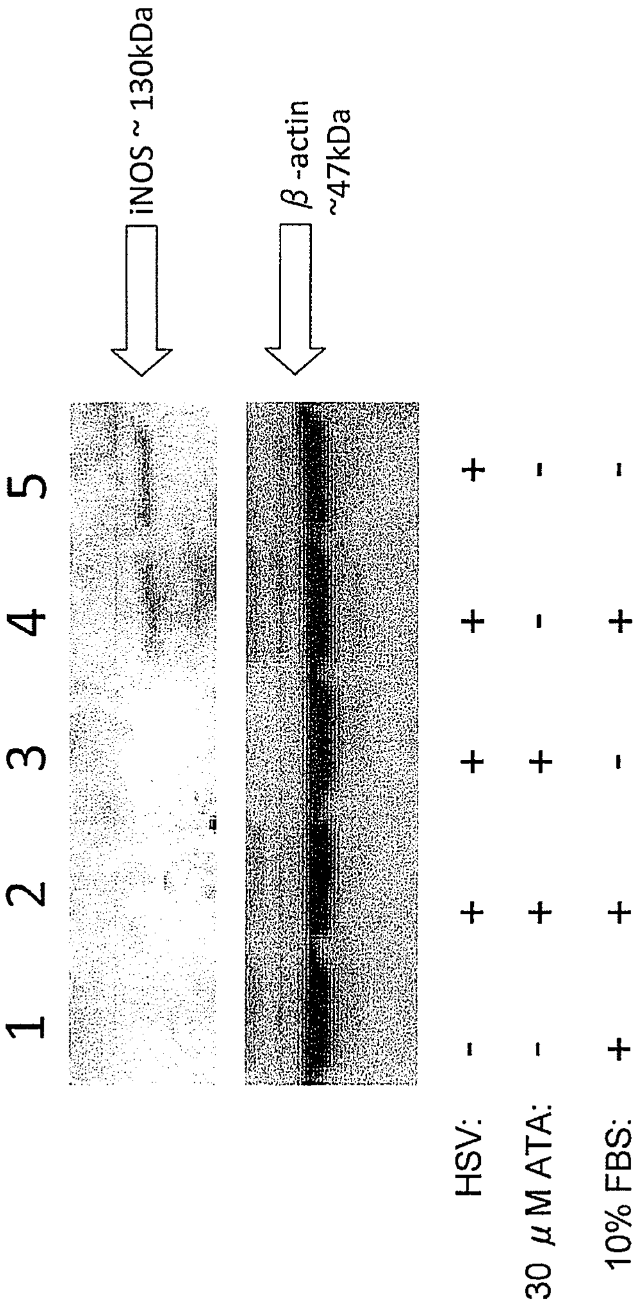
FIG. 1 is a representation of a Western blot showing that aurintricarboxylic acid (ATA) inhibits iNOS expression in d27-1-infected V27 lysates.

The practice of the present invention will employ, unless otherwise indicated, conventional methods of chemistry, biochemistry, recombinant DNA techniques and immunology, within the skill of the art. Such techniques are explained fully in the literature. See, e.g., *Fundamental Virology,* 2nd Edition, vol. I & II (B. N. Fields and D. M. Knipe, eds.); *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entirety.

1. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a herpesvirus" includes a mixture of two or more such viruses, and the like.

The terms "recombinant HSV," "rHSV," and "rHSV vector" refer to isolated, genetically modified forms of herpes simplex virus (HSV) containing heterologous genes incorporated into the viral genome. By the term "rHSV/rc" or "rHSV/rc virus" or "rHSV helper function vector" is meant a rHSV in which the AAV rep and/or cap genes have been incorporated into the rHSV genome. The terms "rHSV expression virus," and "rHSV/AAV" denote a rHSV in which inverted terminal repeat (ITR) sequences from AAV have been incorporated into the rHSV genome.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification. Depending on the expression system used, a polypeptide may include or lack an N-terminal methionine. Additionally, a polypeptide may or may not include the native signal sequence, if one is naturally present. If a signal sequence is not normally present, the protein can be produced with a heterologous sequence.

A "native" polypeptide refers to a polypeptide having the same amino acid sequence as the corresponding molecule derived from nature. Such native sequences can be isolated from nature or can be produced by recombinant or synthetic means. The term "native" sequence specifically encompasses naturally-occurring truncated or secreted forms of the specific molecule (e.g., an extracellular domain sequence), naturally-occurring variant forms (e.g., alternatively spliced forms) and naturally-occurring allelic variants of the polypeptide.

By "variant" is meant an active polypeptide as defined herein having at least about 80% amino acid sequence identity with the corresponding full-length native sequence, a polypeptide lacking the signal peptide, an extracellular domain of a polypeptide, with or without a signal peptide, or any other fragment of a full-length polypeptide sequence as disclosed herein. Such polypeptide variants include, for instance, polypeptides wherein one or more amino acid residues are added, or deleted, at the N- and/or C-terminus of the full-length native amino acid sequence. Ordinarily, a variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to the corresponding full-length native sequence. Ordinarily, variant polypeptides are at least about 10 amino acids in length, such as at least about 20 amino acids in length, e.g., at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

Particularly preferred variants include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 or 50 conservative or non-conservative amino acid substitutions, or any number between 5-50, so long as the desired function of the molecule remains intact.

"Homology" refers to the percent identity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National Biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are well known in the art.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning, supra; Nucleic Acid Hybridization*, supra.

By the term "degenerate variant" is intended a polynucleotide containing changes in the nucleic acid sequence thereof, that encodes a polypeptide having the same amino acid sequence as the polypeptide encoded by the polynucleotide from which the degenerate variant is derived.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

By "vector" is meant any genetic element, such as a plasmid, phage, transposon, cosmid, chromosome, virus, virion, etc., which is capable of replication when associated with the proper control elements and which can transfer gene sequences to cells. Thus, the term includes cloning and expression vehicles, as well as viral vectors.

By "recombinant vector" is meant a vector that includes a heterologous nucleic acid sequence which is capable of expression in vivo.

By "recombinant virus" is meant a virus that has been genetically altered, e.g., by the addition or insertion of a heterologous nucleic acid construct into the particle.

The term "transgene" refers to a polynucleotide that is introduced into a cell and is capable of being transcribed into RNA and optionally, translated and/or expressed under appropriate conditions. In one aspect, it confers a desired property to a cell into which it was introduced, or otherwise leads to a desired therapeutic or diagnostic outcome.

The terms "genome particles (gp)," and "genome equivalents," as used in reference to a viral titer, refer to the number of virions containing the recombinant AAV DNA genome, regardless of infectivity or functionality. The number of genome particles in a particular vector preparation can be measured by procedures known in the art, such as described in for example, in Clark et al., *Hum. Gene Ther.* (1999) 10:1031-1039; and Veldwijk et al., *Mol. Ther.* (2002) 6:272-278.

The terms "infection unit (iu)," "infectious particle," or "replication unit," as used in reference to a viral titer, refer to the number of infectious recombinant AAV vector particles as measured by the infectious center assay, also known as replication center assay, as described, for example, in McLaughlin et al., *J. Virol.* (1988) 62:1963-1973.

The term "transducing unit (tu)" as used in reference to a viral titer, refers to the number of infectious recombinant AAV vector particles that result in the production of a functional transgene product as measured in functional assays such as described in, for example, in Xiao et al., *Exp. Neurobiol.* (1997) 144:1 13-124; or in Fisher et al., *J. Virol.* (1996) 70:520-532 (LFU assay).

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) *Virology,* 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties into suitable host cells.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "nucleic acid" sequence refers to a DNA or RNA sequence. The term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxy-amino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

By "isolated" when referring to a protein or nucleotide sequence, is meant that the indicated molecule is present in the substantial absence of other biological macromolecules of the same type. Thus, for example, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3-prime (3')" or "5-prime (5')" relative to another sequence, it is to be understood that it is the position of the sequences in the "sense" or "coding" strand of a DNA molecule that is being referred to as is conventional in the art.

The term "about", particularly in reference to a given quantity, is meant to encompass deviations of plus or minus five percent.

2. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Central to the present invention is the discovery that aurintricarboxylic acid (ATA) in micromolar concentrations increases HSV-1 vector yield. This finding is important for both large-scale HSV production, as well as rHSV and rAAV vector production. Moreover and surprisingly, as shown in the examples, the presence of ATA in rHSV-1 stocks did not negatively influence rAAV yield. This result is surprising as ATA in millimolar amounts and higher concentrations is known to be an antiviral agent (Cushman et al., *J. Med. Chem.* (1991) 34:329-337; Zhang et al., Antiviral Res. (1999) 43:23-35; Yap et al., *Computational Biol. and Chem.* (2005) 29:212-219; De Clercq, *Advents, Advances, and Adventures Med. Res. Rev.* (2011) 31:118-160).

As explained above, investigators have reported antiviral activity of nitric oxide (NO) against several viruses such as vaccinia virus, vesicular stomatitis virus, and Japanese encephalitis virus, among others (Bi et al., *J. Virol.* (1995) 69:6466-6472; Harris et al., *J. Virol.* (1995) 69:910-915; Lin et al., 1997; Pertile et al., *Avian Dis.* (1996) 40:342-348). NO is a free radical gaseous molecule is a mediator of host defense (Croen K. D., *J. Clin. Invest.* (1993) 91:2446-2452; Karupiah et al., *Science* (1993) 261:1445-1448; Rolph et al., *Virol.* (1996) 217:470-477; Amaro et al., *J. Med. Virol.* (1997) 51:326-331; Lane et al., *J. Virol.* (1997) 71:2202-2210). HSV infection is capable of inducing the expression of inducible nitric oxide synthase (iNOS), a gene encoding an inducible isoform of NOS that produces large amounts of NO.

As shown herein, ATA suppresses HSV-up-regulated iNOS and thereby increases HSV titers in culture. Additional iNOS inhibitors, including dexamethasone and valproic acid, also have the same effect. In one embodiment, then, the use of such iNOS inhibitors increases recombinant herpesvirus titers in culture, allowing the production of significantly more virus than produced in the absence of the particular inhibitor. Viruses produced by the method can be used in a variety of contexts, including for prophylactic, therapeutic and diagnostic purposes, as well as for producing recombinant constructs in sufficient quantity to use in the preparation of recombinant virions for gene delivery and gene therapy.

Aurintricarboxylic acid (ATA), 5-((3-carboxy-4-hydroxyphenyl)(3-carboxy-4-oxo-2,5-cyclohexadien-1-ylidene) methyl)-2-hydroxybenzoic acid, is a heterogeneous mixture of nonsulfated negatively-charged aromatic polymers that forms when salicylic acid is treated with formaldehyde, sulfuric acid and sodium nitrite (see Cushman, et al., (1991) *J. Med. Chem.* 34:329-337; Cushman, et al., *J. Med. Chem.* 34:337-342). Aurintricarboxylic acid has the formula:

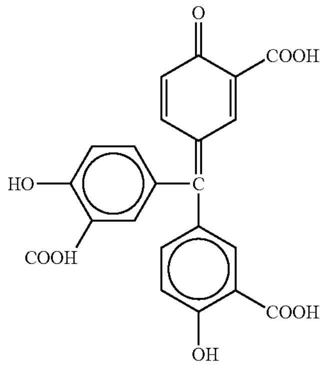

The heterogeneous mixture of ATA was described to inhibit protein nucleic acid interactions (Gonzalez et al., *Biochim. Biophys. Acta,* (1979) 562:534-545); to interact with steroid receptors at the nuclear uptake and the nuclear binding levels (Mellon, W. S., *Biochem. Pharmacol.* (1984) 33:1047-1057; Moudgil et al., *J. Steroid Biochem.* (1985) 23:125-132); to inhibit DNA polymerase (Nakane et al., *Eur. J. Biochem.* (1988) 177:91-96); and to act as a RNAase inhibitor (Skidmore et al., *Biochem. J.* (1989) 263:73-80).

ATA for addition to virus in culture can be used in the acidic form or can be provided as a salt, such as aurintricarboxylic acid trisodium salt; calcium salt; ammonium salt, etc.

Additional substances that will find use with the present methods include dexamethasone (Dex) and valproic acid (VA). Dex has been shown to inhibit iNOS expression in rat mesangial cells at transcriptional and post-transcriptional levels (Kunz et al., *Biochem. J.* (1994) 304:337-340; Kunz et al., *Proc. Natl. Acad. Sci. USA* (1996) 93:255-259). Dex has also been shown to enhance HSV-1 oriL DNA replication in PC12 cells. Sodium valproate, the sodium salt of VA, has been shown to stimulate replication of HSV-1, human cytomegalovirus, HIF-1, human herpes virus-8, measles virus and poliovirus type 1 (Motamedifar et al., *Iran. J. Med. Sci.* (2006) 31:28-32; Kuntz-Simon et al., *J. Gen. Virol* (1995) 76:1409-1415; Moog et al., *J. Gen. Virol* (1996) 77:1993-1999; Ylisastigui et al., *AIDS* (2004) 18:1101-1108; Shaw et al., *AIDS* (2000) 14:899-902; Kabiri et al. *Iran J. Med. Sci.* (2001) 26:55-61). Additionally, valproic acid has been shown to inhibit iNOS (Guo et al., *Surgery* (2007) 142:156-162). As with ATA, VA, or its salts, such as sodium, calcium, ammonium salts, etc., can be used in the present methods.

Although the use of ATA, Dex, and VA to produce rHSV-1 vectors at higher titers is exemplified herein, these iNOS inhibitors can be used to increase the titer of a variety of viruses in culture, such as but not limited to viruses of the families Adenoviridae, Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Poxviridae; Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; the various hepatitis viruses, such as HAV, HBV and HCV; papilloma viruses and rotaviruses; retroviruses; etc. See, e.g. Virology, 3rd Edition (W. K. Joklik ed. 1988); *Fundamental Virology,* 2nd Edition (B. N. Fields and D. M. Knipe, eds. 1991), for a description of these and other viruses. These viruses, or immunogens derived therefrom, can be used in the production of vaccines and diagnostics. Moreover, some of these viruses, and in particular, the herpesviruses, can be used to produce recombinant vectors for the production of recombinant virions for use in gene delivery techniques described below.

Thus, ATA, Dex and VA can be used to increase the yield of any of the herpesviruses that are members of the family herpesviridae. This includes equine herpes virus, bovine herpes virus (BHV) and human herpes simplex virus (HSV) types 1 and 2, such as BHV-1, BHV-2, HSV-1 and HSV-2, varicella zoster virus (VZV), Epstein-Barr virus (EBV), cytomegalovirus (CMV), HHV6 and HHV7, among others. The herpesviruses can be derived from any of the many strains. For example, when the virus produced using the invention is HSV, the virus may be derived from, for example, HSV-1 or HSV-2, and may be from any of the various HSV strains, such as HSV-1 strain KOS, HSV-1 strain McIntyre, HSV-1 strain Patton, HSV-2 strain 333, HSV-2 strain G, and the like. Moreover, the viruses produced may be either wild-type viruses, or derivatives thereof, including recombinant viruses and inter-type recombinants containing DNA from HSV-1 and HSV-2. Derivatives preferably have at least 70% sequence homology to either the HSV-1 or HSV-2 genomes or portions thereof, more preferably at least 80%, even more preferably at least 90 or 95%. A derivative may have the sequence of a HSV-1 or HSV-2 genome modified by nucleotide substitutions, for example from 1, 2 or 3 to 10, 25, 50 or 100 substitutions. The HSV-1 or HSV-2 genome may alternatively or additionally be modified by one or more insertions and/or deletions and/or by an extension at either or both ends.

Other derivatives include strains that already have mutations in genes, particularly mutations in genes that result in attenuation of the virus. Examples of such viruses include strain 1716 (MacLean et al., *J. Gen. Virol.* (1991) 72:632-639), strains R3616 and R4009 (Chou and Roizman, *Proc. Natl. Acad. Sci USA* (1992) 89: 3266-3270) and R930 (Chou et al., *J. Virol.* (1994) 68:8304-8311) all of which have mutations in ICP34.5, strain d120 which has a deletion in ICP4 (DeLuca et al., *J. Virol.* (1985) 56:558-570), strain d27-1 (Rice and Knipe, *J. Virol.* (1990) 64:1704-1715) which has a deletion in ICP27) or strain d92 which has deletions in both ICP27 and ICP4 (Samaniego et al., *J. Virol.* (1995) 69:5705-5715). The terminology used in describing the various HSV genes is as found in, e.g., Coffin and Latchman (1996), In: Genetic Manipulation of the Nervous System (DS Latchman Ed.) pp 99-114: Academic Press, London.

As is readily apparent, any rHSV suitable for the intended purpose can be used in the invention. In certain embodiments, the rHSV used in the invention is replication-defective. For the production of rAAV virions, infection of producer cells with rHSV that is incapable of replication is preferred because in contrast to methods involving use of adenovirus, the rHSV does not become a significant contaminant of the rAAV product. This can serve to increase the final yield of rAAV virions by eliminating purification steps associated with removal of adenovirus. In a particular embodiment of the invention, the rHSV is constructed from a mutant of HSV-1 in which the inability to replicate is due to a deletion in the ICP27 gene. Any other suitable mutants of HSV exhibiting a replication-defective phenotype can also be used to construct the rHSV.

One particularly preferred recombinant mutant HSV-1 strain for rAAV production using the subject methods is HSV-1 strain d27-1. This strain can be prepared as described in e.g., Conway et al., *Gene Ther.* (1999) 6:973 985 and U.S. Pat. No. 7,091,029, incorporated herein by reference in its entirety. As explained above, this mutant vector does not produce ICP27 and is advantageously used to produce rAAV virions as host cell splicing of messenger RNA is known to be inhibited by ICP27. ICP27 may also effect appropriate splicing of the AAV-2 rep and cap messages. This vector is replication defective and shows reduced cytotoxicity compared with wild type (wt) HSV-1. The virus d27-1 displays several other features that are advantageous for use as a helper virus for rAAV virion production. First, it expresses the early genes known to be required for rAAV production (Weindler et al., *J. Virol.* (1991) 65:2476-2483). In addition, d27.1 over-expresses ICP8, the single-stranded DNA binding protein that is the product of UL29, one of the HSV-1 genes essential for AAV replication and packaging (Weindler et al., *J. Virol.* (1991) 65:2476-2483).

The AAV genome is a linear, single-stranded DNA molecule containing about 4681 nucleotides. The AAV genome generally comprises an internal, nonrepeating genome flanked on each end by inverted terminal repeats (ITRs). The ITRs are approximately 145 base pairs (bp) in length. The ITRs have multiple functions, including providing origins of DNA replication, and packaging signals for the viral genome. The internal nonrepeated portion of the genome includes two large open reading frames, known as the AAV replication (rep) and capsid (cap) genes. The rep and cap genes code for viral proteins that allow the virus to replicate and package into a virion. In particular, a family of at least four viral proteins are expressed from the AAV rep region, Rep 78, Rep 68, Rep 52, and Rep 40, named according to their apparent molecular weight. The AAV cap region encodes at least three proteins, VPI, VP2, and VP3.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. For a description of the AAV rep coding region, see, e.g., Muzyczka, N. (1992) *Current Topics in Microbiol. and Immunol.* 158:97-129; and Kotin, R. M. (1994) *Human Gene Therapy* 5:793-801. Suitable homologues of the AAV rep coding region include the human herpesvirus 6 (HHV-6) rep gene which is also known to mediate AAV-2 DNA replication (Thomson et al. (1994) *Virology* 204:304-311).

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome. For a description of the AAV cap coding region, see, e.g., Muzyczka, N. and Kotin, R. M. (supra).

Typically two rHSV vectors will be used to produce rAAV virions. One is a rHSV helper function vector in which the AAV rep and/or cap genes have been incorporated into the rHSV genome. The other is a rHSV expression vector in which ITR sequences from AAV have been incorporated into the rHSV genome and flank a gene of interest.

Thus, in one embodiment, the iNOS inhibitor can be used to increase the yield of a first rHSV vector that contains the AAV rep and/or cap genes. Embodiments of the first rHSV vector of the method include but are not limited to gene constructs based on the cap gene found in various serotypes of AAV including AAV-1, AAV-2, AAV-3, AAV-4, AAV-5 and AAV-6, AAV-7 and AAV-8, caprine and bovine AAV (see, e.g., U.S. Publ. No. 20080292595, incorporated herein by reference in its entirety), and variants thereof. Also within the scope of the invention are rep and cap genes from novel AAV serotypes, and those modified by recombination or mutation of existing serotypes. The rep and cap genes of the AAV helper function vector can be derived from any of the known AAV serotypes, as explained above. For example, the rHSV helper function vector may have a rep gene derived from AAV-2 and a cap gene derived from AAV-6; one of skill in the art will recognize that other rep and cap gene combinations are possible, the defining feature being the ability to support rAAV virion production.

In certain embodiments, the AAV rep and cap genes in the rHSV helper function vector may be driven by their native promoters. The p5 and p19 promoters of AAV-2 control expression of Rep 78 and 68 and Rep 52 and 40, respectively. The p40 promoter controls expression of VP1, VP2 and VP3. Additionally, heterologous promoters may be used to drive expression of the AAV genes. Examples of other promoters that can be used in the disclosed methods include but are not limited to the SV40 early promoter, CMV promoter, HSV-1 thymidine kinase (HSV-1 tk) promoter, metallothionine inducible promoter, mouse mammary tumor virus promoter and chicken β-actin promoter.

The gene construct can be inserted into any site or sites in the HSV genome suitable for integration of the rep and cap genes. In certain embodiments, the vector is constructed by homologous recombination of the AAV rep and cap genes into the thymidine kinase (tk) locus of the rHSV-1 virus, as described in Conway et al., *Gene Ther.* (1999) 6:986-993 and U.S. Pat. No. 7,091,029, incorporated herein by reference in its entirety.

As explained herein, the rHSV helper function vector encodes the "AAV helper function" sequences (i.e., rep and cap), which function in trans for productive AAV replication and encapsidation. Preferably, the rHSV helper function vector supports efficient rAAV virion production without generating any detectable wt AAV virions (i.e., AAV virions containing functional rep and cap genes). An example of such a vector is rHSV-1 d27.1rc. The vector and methods of producing the same are described herein in the examples, as well as in Conway et al., *Gene Ther.* (1999) 6:986-993; and U.S. Pat. No. 7,091,029, incorporated herein by reference in its entirety.

The second rHSV vector is termed a rHSV expression vector and contains ITRs from AAV with one or more genes of interest driven by one or more promoters. In some embodiments, the gene of interest is inserted between a pair of ITRs. The heterologous gene is typically functionally linked to a heterologous promoter (constitutive, cell-specific, or inducible) capable of driving gene expression in the patient's target cells under appropriate conditions. Termination signals, such as polyadenylation sites, can also be included.

The nucleotide sequences of AAV ITR regions are known. See, e.g., Kotin, R. M. (1994) *Human Gene Therapy* 5:793-801; Berns, K. I. "Parvoviridae and their Replication" in *Fundamental Virology,* 2nd Edition, (B. N. Fields and D. M. Knipe, eds.) for the AAV-2 sequence. AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV-1, AAV-2, AAV-3, AAV-4, AAV-5, AAV-6, AAV-7 and AAV-8, caprine and bovine AAV (see, e.g., U.S. Publ. No. 20080292595. incorporated herein by reference in its entirety), and variants thereof. Furthermore, 5' and 3' ITRs which flank a selected nucleotide sequence in an expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV rep gene products are present in the cell.

AAV ITRs can be excised from the viral genome or from an AAV vector containing the same and fused 5' and 3' of a selected nucleic acid construct using standard ligation techniques, such as those described in Sambrook et al., supra. For example, ligations can be accomplished in 20 mM Tris-Cl pH 7.5, 10 mM MgCl2, 10 mM DTT, 33 μg/ml BSA, 10 mM-50 mM NaCl, and either 40 μM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 μg/ml total DNA concentrations (5-100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

The selected polynucleotide sequence is operably linked to control elements that direct the transcription or expression thereof in a subject's cells. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, neuron-specific enolase promoter, a GFAP promoter, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.), Invivogen (San Diego, Calif.) and others.

The gene of interest may be a gene likely to be of therapeutic value. Examples of therapeutic genes include but are not limited to α-1 antitrypsin, Factor VIII, Factor IX, GAA, erythropoietin and PEDF. When it is desirable to select for or to identify successful transgene expression, the gene of interest may be a reporter gene. Many examples of genes used as reporters or for selection are known, and can be used in the invention. These include but are not limited to the genes encoding β-galactosidase, neomycin, phosphoro-transferase, chloramphenicol acetyl transferase, thymidine kinase, luciferase, beta-glucuronidase, aminoglycoside, phosphotransferase, hygromycin B, xanthine-guanine phosphoribosyl, luciferase, DHFR/methotrexate, and green fluorescent protein (GFP).

The rHSV-1 expression virus can be produced in much the same manner as described above, namely, by homologous recombination into the HSV-1 tk gene, as described in, e.g., Conway et al., *Gene Ther.* (1999) 6:986-993 and U.S. Pat. No. 7,091,029, incorporated herein by reference in its entirety.

Once produced, the rHSV vectors, or any other virus of interest, is propagated in culture in an appropriate cell line. For herpesviruses, such cell lines include, but are not limited to, Vero cells, 293 cells, HeLa cells, and the like, available from the American Type Culture Collection, Rockville, Md. If the HSV-1 d27.1 vector is used, this virus will typically be cultured in the ICP27-complementing cell line V27 (Rice et al., *J. Virol.* (1990) 64:1704-1715). Any suitable medium for the virus in question, with or without serum, such as fetal bovine serum, can be used, such as but not limited to RPMI 1640 medium, Dulbecco's Modified Eagles Medium (DMEM), F12 medium or a mixture of the latter (DF medium). If serum is present, the culture can include, for example 2% to 20% serum, more typically 5% to 15% serum, 7% to 12% serum, or any number within these ranges, such as 5%, 6%, 7%, 8%, 9%, 10%, 11%, 12%, 13%, 14%, 15%, and the like. Moreover, if serum is used, it can be present in the initial culture, and/or in subsequent fresh media added to the cultures.

The amount of the iNOS inhibitor to be added in the method according to the invention can be varied and is to a certain extent dependent on the particular inhibitor used, the medium used and the virus to be cultured. For example, when herpesviruses are cultured in Vero cells, the concentration of ATA in the initial culture, if present, will typically be 5 μM to 500 μM, preferably 10 μM to 250 μM, such as 20 μM to 100 μM, i.e., 30 μM to 75 μM, such as 30 . . . 35 . . . 40 . . . 45 . . . 50 . . . 55 . . . 60 . . . 65 . . . 70 . . . 75, etc. or any integer within these stated ranges. Similarly, the concentration of dexamethasone if present in the initial culture will typically be. 1 μM to 500 μM, preferably 0.5 μM to 250 μM, such as 1 μM to 100 μM, i.e., 5 μM to 75 μM, such as 1 . . . 5 . . . 15 . . . 10 . . . 20 . . . 25 . . . 30 . . . 35 . . . 40 . . . 45 . . . 50 . . . 55 . . . 60 . . . 65 . . . 70 . . . 75, etc. or any integer within these stated ranges. If valproic acid is used, the initial concentration will be 0.1 mM to 500 mM, preferably 0.5 mM to 250 mM, such as 1 mM to 100 mM, i.e., 5 mM to 75 mM, such as 1 . . . 5 . . . 15 . . . 10 . . . 20 . . . 25 . . . 30 . . . 35 . . . 40 . . . 45 . . . 50 . . . 55 . . . 60 . . . 65 . . . 70 . . . 75, etc. or any integer within these stated ranges.

In certain embodiments, virus-infected cells are initially cultured in media as described above for 0.5 hours to 24 hours, such as 0.75 hours to 12 hours, 1 hour to 5 hours, 1 hour to 2 hours, or any number of hours or fractions thereof within these ranges. The iNOS inhibitor and/or serum may or may not be present in the initial culture. Fresh media is subsequently added and cultures incubated for 24 to 120 hours, such as 48 to 96 hours, 50 to 80 hours, 60 to 75 hours, 70 to 74 hours, or any number of hours or fractions thereof within these ranges. The iNOS inhibitor and/or serum may or may not be present in the subsequence culture, with the proviso that the iNOS inhibitor is present in either one or both of the initial culture and the subsequent culture.

In some embodiments, the iNOS inhibitor in the initial culture is present at a higher concentration than in the subsequent culture. Thus, for example, if the iNOS inhibitor is ATA, it can be present in an amount of 30 to 75 μM in the initial culture and then 5 to 25 μM in the subsequent culture. Alternatively, the inhibitor can be present only in the initial or the subsequent culture.

As shown in the examples below, one particularly preferred method using ATA includes the presence of 50 μM ATA in the initial culture, with a reduction in the amount of ATA in the subsequent culture to 20 μM. Additionally, in the case of ATA, it is preferable to include serum at the same time that ATA is present. Thus, if ATA is added to the initial culture, it is advantageous to add fetal bovine serum (FBS) to the media. Likewise, if ATA is added to the subsequent culture, the addition of FBS is necessary to obtain higher viral yields.

The viruses are then cultured to obtain a desirable titer of virus. For example, in the case of the HSV-1 d27-1 vectors described herein, ATA increases the d27-1 yields in V27 cells supernatants 3-5 times and the titers can be at least $1\times10^8$ PFU/ml or $4\times10^8$ DRP/ml. Similarly, ATA also increases the yields of wild type (wt) HSV-1 viruses strains McIntyre and KOS by 1 log, and the 293 or Vero titers can be up to $1\times10^9$ DRP/ml. The viruses are then harvested for further use.

For the purposes of the invention, suitable host cells for producing rAAV virions include microorganisms, yeast cells, insect cells, and mammalian cells, that can be, or have been, used as recipients of a heterologous DNA molecule and that are capable of growth in, for example, suspension culture, flasks, plates, a bioreactor, or the like. The term includes the progeny of the original cell which has been transfected. Thus, a "host cell" as used herein generally refers to a cell which has been transduced with an exogenous DNA sequence. If recombinant herpesviruses are produced in one type of cells for use in making rAAV virions, the harvested vectors are then transfected into another suitable host cell. 293 cells, originated from a stable human cell line, (readily available through, e.g., the American Type Culture Collection under Accession Number ATCC CRL1573) are preferred host cells to produce rAAV virions. Particularly, the human cell line 293 is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The 293 cell line is readily transfected, and provides a particularly convenient platform in which to produce rAAV virions.

AAV helper functions are introduced into the host cell by transducing the host cell with a rHSV helper function construct either prior to, or concurrently with, using the rHSV expression vector. rHSV helper constructs are thus used to provide at least transient expression of AAV rep and/or cap genes to complement missing AAV functions that are necessary for productive AAV infection. AAV helper constructs lack AAV ITRs and can neither replicate nor package themselves.

Following recombinant AAV replication, rAAV virions can be purified from the host cell using a variety of conventional purification methods, such as column chromatography, CsCl gradients, and the like. For example, a plurality of column purification steps can be used, such as purification over an anion exchange column, an affinity column and/or a cation exchange column. See, for example, International Publication No. WO 02/12455.

The resulting rAAV virions containing the nucleotide sequence of interest can then be used for gene delivery using techniques well known in the art and described in e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., *Molec. Cell. Biol.* (1988) 8:3988-3996; Vincent et al., *Vaccines* 90 (1990) (Cold Spring Harbor Laboratory Press); Carter, B. J. *Current Opinion in Biotechnology* (1992) 3:533-539; Muzyczka, N. *Current Topics in Microbiol. and Immunol.* (1992) 158:97-129; Kotin, R. M. *Human Gene Therapy* (1994) 5:793-801; Shelling and Smith, *Gene Therapy* (1994) 1:165-169; and Zhou et al., *J. Exp. Med.* (1994) 179:1867-1875.

2. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

Cells

Vero-derived V27 cells (Rice et al., *J. Virol.* (1989) 63:3399-3407) and human embryonic kidney cells (HEK)-derived 293 cells (Graham et al., *J. Gen. Virol.* (1977) 36:59-74) were obtained from the Applied Genetic Technologies Corporation (AGTC, Alachua, Fla.), Vero and HeLa cells were purchased from American Type Culture Collection (ATCC, Manassas, Va.). All cells were maintained in Dulbecco's modified Eagle's medium (DMEM; HyClone, South Logan, Utah) containing 10% fetal bovine serum (FBS; HyClone) and either Geneticin (50 mg/ml; Invitrogen) for V27 cells or 1% penicillin/streptomycin (Cellgro Mediatech, Manassas, Va.) for the other cells.

HSV-1 Production

The wtHSV-1 KOS strain and the ICP27-deficient derivatives of the wtHSV-1 KOS strain: vectors d27-1 (Rice and Knipe, *J. Virol.* (1990) 64:1704-1715), rHSV-rep2/cap2 and rHSV-EGFP (Kang et al., *Gene Ther.* (2009) 16:229-239) and their producer ICP27-complementing V27 cell line were obtained from AGTC (Alachua, Fla.). The wtHSV-1 MacIntyre strain, purchased from Advanced Biotechnologies Inc. (ABI, Columbia Md.) and wtHSV-1 KOS strain were propagated in Vero, 293 or HeLa cell lines. Infectious vector particles were harvested 72 hr postinfection by recovering culture supernatant. The titers of HSV-1 stocks in DNase resistant particles/ml (DRP/ml) were determined by Taqman assay. Viral genomes within crude culture medium were quantified via treatment in the presence of DNase I (50 U/ml final; Promega) at 37° C. for 60 min, followed by proteinase K (Invitrogen) digestion (1 U/ml) at 50° C. for 60 min, and then denatured at 95° C. for 30 min. Linearized plasmid pZero 195 UL36 (obtained from AGTC, Inc., Alachua, Fla.) was used to generate standard curves. The primer-probe set was specific for the vector genome UL36 sequence (HSV-UL36 F: 5'-GTTGGTTATGGGG-GAGTGTGG (SEQ ID NO:1); HSV-UL36 R: 5'-TCCTTGTCTGGGGTGTCTTCG (SEQ ID NO:2); HSV-UL36 Probe: 5'-6FAM-CGACGAA-GACTCCGACGCCACCTC-TAMRA (SEQ ID NO:3). Amplification of the PCR product was achieved with the following cycling parameters: 1 cycle at 50° C. for 2 min, 1 cycle at 95° C. for 10 min; 40 cycles of 95° C. for 15 sec, and 60° C. for 60 sec.

ATA Experiments

ATA (Sigma-A1895 Aurintricarboxylic acid practical grade, ≥85% (titration), powder) stock solution was generated as 500 μM concentration in 100 mM sodium bicarbonate water solution. ATA stock solution was further diluted in DMEM+/−10% fetal bovine serum (FBS, Hyclone, Waltham, Mass.) into concentration ranges of 12-60 μM ATA (8.5-21 μgATA/ml). The HSV-1 infection at multiplicity of infection of 0.15 (MOI=0.15) (typically $6\times10^5$ cells in a 6-well plate) was performed in 40% (⅖ vol) of the total final media volume for 1-2 hrs and the remaining media (60% or ⅗ of the total final volume) was added during the dilution step. The cells were then incubated 72 hours and supernatant harvested to perform forming units per milliliter (PFU/ml) and DRP/ml titer assays.

Dexamethasone(Dex) Experiments

Dexamethasone (Sigma-D4902) was dissolved to 2 mg/ml in absolute alcohol. This was diluted with DMEM to achieve a 1M concentration and stored at −20° C.

V27 cells were seeded into six well plates the day prior to infection at $6\times10^5$ cells/well. Dexamethasone was added to achieve a concentration of 1 μM into the seeding media. This was mixed well and added to the wells.

Media was aspirated and infectious HSV-1 d27-1 stock was added at MOI 0.15 (=cell seed density×0.15/pfu titer of HSV stock) per 1 ml of DMEM (no additives). 1 ml of infectious inoculum was added per well. This was incubated for 1-2 hours at 37° C., 5% $CO_2$ incubator, after which time 1.5 ml of DMEM-10% FBS was added. The cultures were returned to the incubator for 70-74 hours.

Free media was harvested, vortexed, centrifuged at 1,100×g for 10 minutes at 4° C. Supernatant was transferred to a new dispensing tube, vortexed, aliquoted and stocks were frozen at −80° C.

Valproic Acid (VA) Experiments

Valproic acid (Sigma-P4543) was dissolved to 1 M concentration in water. V27 cells were seeded into six well plates the day prior to infection at $6\times10^5$ cells/well. 1 M valproic acid was spiked into 1 ml DMEM-10% FBS to achieve a concentration of 5 μM. This was vortexed well and added to the wells. Plates were incubated for six hours, aspirated and infectious HSV-1 d27-1 stock added at MOI 0.15 (=cell seed density×0.15/pfu titer of HSV stock) per 1 ml of DMEM (no additives).

1 ml of infectious inoculum was added per well and incubated for 1-2 hours at 37° C., 5% $CO_2$ incubator after which time 1.5 ml of DMEM-10% FBS was added. The plates were returned to the incubator for 70-74 hours. Free media was harvested, vortexed, and centrifuged at 1,100×g for 10 minutes at 4° C. Supernatant was transferred to a new dispensing tube, vortexed, and aliquoted. Stocks were frozen at −80° C.

rAAV Production 293 cells ($2.5\times10^6$) were simultaneously co-infected with both rHSV-rep2/cap2 and rHSV-EGFP vectors as described by Kang et al., *Gene Ther* (2009) 16:229-239. At 2-4 hr post infection, infectious medium was exchanged with DMEM+10% FBS equivalent to double the preinfection culture volume. At the time of harvest, the cell pellet was frozen at −80° C. DRP titers were quantified by real-time polymerase chain reaction (qPCR) in a96-well block thermocycler (Applied Biosystems; 7500 Real Time PCR system). Crude samples were subjected to three cycles of freezing and thawing, then incubated in the presence of Benzonase (250 U/ml), 2 mM $MgCl_2$, 1% final concentration protein grade Tween 80 (Calbiochem) and incubated at 37° C. for 60 min, followed by 0.25% Trypsin (Gibco) digestion at 50° C. for 60 min. Finally, treatment with DNase I (50 U/ml; Promega) at 37° C. for 30 min, and then denatured at 95° C. for 20 min. Linearized plasmidpDC67/+SV40 was used to generate standard curves. The primer-probe set was specific for the simian virus 40 (SV40) poly(A) sequence: rAAV-F: 5'-AGCAATAGCATCACAAATTTCACAA-3' (SEQ ID NO:4); rAAV-R: 5'-GCAGACATGATAAGATACATTGAT-GAGTT-3' (SEQ ID NO:5); rAAV-Probe: 5' 6-FAM-AG-CATTTTTTTCACTGCATTCTAGTTGTGGTTTGTC-TAMRA-3' (SEQ ID NO:6). Amplification of the PCR product was achieved with the following cycling parameters: 1 cycle at 50° C. for 2 min, 1 cycle at 95° C. for 10 min; 40 cycles of 95° C. for 15 sec, and 60° C. for 60 sec.

Human Genome Array

Confluent 293 cells ($2.4\times10^6$ cells in a 75 $cm^2$ flask) were cultured in DMEM+10% FCS for approximately 20 hrs and were then infected with one plaque forming unit per cell (PFU/cell) of HSV-1 MacIntyre Strain for 90 min. ATA at a concentration 20 μM (final) was added 90 min post-infection. The infected cells were harvested at 24 h after infection. Total RNA of sufficient quality and quantity was isolated from suspension using RNeasy Plus Mini Kit (QIAGEN, Valencia, Calif.) according to the manufacturer's instructions. Whole genome expression profiling was performed on Affymetrix Human U133 Plus 2.0 Array by the Asuragen, Inc. 3 μg total RNA was provided as input material.

Overall, RNA quality assessed on the bioanalyzer had RIN values of >9. Array hybridization and scaling factors were within passing quality control range. After scanning, raw expression CEL files were processed with Affymetrix Expression Console vs.1.1.2 (affymetrix.com). Each CEL file was processed with Robust Multichip Analysis (RMA) and a summarized table was exported as a text file. All downstream genomics and statistical analyses were done with JMP Genomics (version 5) (jmp.com/software/genomics). First, a filtering step was applied to filter-out low expression, specifically, those values below 6 in $\log^2$ mode in at least 2 out of 8 samples. Out of 54,675 total Affy U133 Plus2 probes, 41,569 (76%) probes remained after the cutoff. Two positive control samples were also seen, human brain and pooled human universal reference RNA, respectively, that hybridized well. For future analysis, these two samples were excluded.

Principle Component Analysis revealed two distinct populations, samples treated with and without HSV. The first principle component separation (91.7%) is therefore explained by the effect of HSV versus Vehicle. Data was median-normalized across each probe to have a median signal of 0. ANOVA was performed to find significant differential transcripts between HSV versus Vehicle, ATA versus Vehicle, HSV+AVA versus Vehicle, and HSV+ATA versus HSV alone. Multiple testing corrections were not included, and significant genes were considered less that p-value of 0.01.

A self-organized map was used to examine patterns of expression among Vehicle, HSV1, and HSV1+ATA. It was desired to find specific transcripts that were either up-regulated or down-regulated by the ATA treatment. A distinct cluster of genes that showed some stimulation in the presence of HSV was found, and ATA correction brought these genes back to vehicle baseline. Similarly, a cluster of genes that were repressed by HSV compared to the vehicle was also found, and subsequently activated by treatment with ATA. These were called Clusters A and B, respectively (see, Tables 1 and 2). Analysis was followed-up to interrogate the biological functions of these clusters using GeneGO software (genego.com).

$RT^2$ Profiler™ PCR Array (SABiosciences-QIAGEN)

6x10e5 293 cells (from AGTC) were infected with wtHSV-1 McIntyre strain at MOI 1 in the presence of DMEM & 10% FBS with or without 50 uM ATA and 1-2 hours and diluted to 40% with DMEM & 10% FBS (final ATA concentration of 20 uM). Triplicate total RNA samples were harvested 24 hrs later using Qiagen RNeasy mini kit and DNase treated on the column and eluted. Eluate RNA triplicate samples were combined and photospectrometer O.D. readings were performed on the eluate at 260 and 280 nm to determine concentration. Sample RNA was converted into template cDNA using SABiosciences RT2 first strand kit. The cDNA was then used in the Human JAK/STAT Signaling Pathway PCR Array (PAHS-039A).

Example 1

Inhibition of HSV-Induced iNOS Levels in V27 Cells Using ATA

V27 cells in Dulbecco's Modified Eagles Medium (DMEM) (Hyclone, Waltham, Mass.) were infected with the HSV-1 d27.1 vector at an MOI of 1 and treated with 30 μM ATA (Sigma, St. Louis, Mo.), with or without 10% fetal bovine serum (FBS). Control experiments without ATA were also performed. V27 cell lysates were obtained 24 hours post infection (h.p.i.) and Western blots were run on the lysates and iNOS protein was detected by using purified rabbit anti-iNOS/NOS Type II pAb (BD Biosciences, Cat#610332). Results are shown in FIG. 1.

As shown, HSV infection induced iNOS expression in those cultures that did not include ATA (lanes 4 and 5). iNOS expression was inhibited in the presence of 30 μM ATA (lanes 2 and 3). The presence or absence of 10% FBS did not have an effect on iNOS expression.

Example 2

Optimization of ATA-HSV Protocol

Figure 2A:
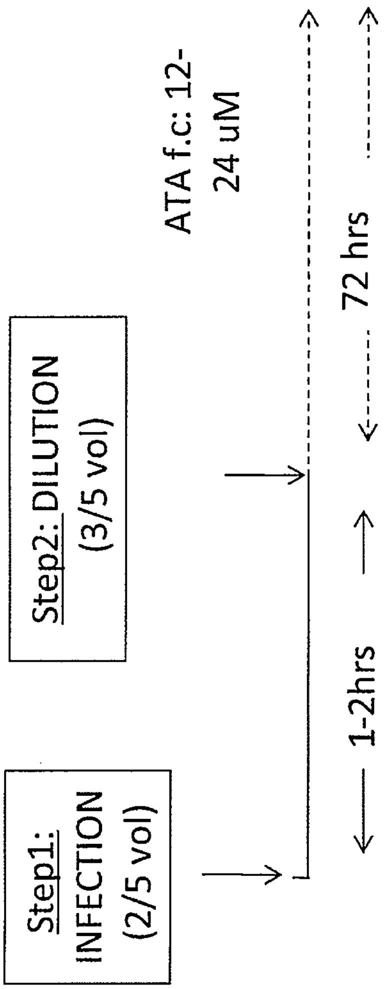
FIGS. 2A-2C show the ATA-HSV protocol rationale (FIG. 2A) and the optimization of d27-1 HSV-1 titers in V27 supernatants in order to determine which concentrations and conditions for ATA addition have impact on HSV yields.

In order to test whether ATA could increase the rHSV-1 d27-1 (d27-1) vector yield in V27 cells, ATA was applied to the media during the infection (Step 1) or dilution steps (Step 2) (FIG. 2A). The d27-1 infection at MOI=0.15 was performed in ⅖ of the final media volume and the remaining ⅗ of the media was added during dilution step.

ATA treatment delayed HSV-1 plaque formation or cell lysis inV27 cell monolayers. Cytopathic effect (CPE) at the time of harvest, 72 hours post-infection, (hpi) was between 20-60% as compared to 100% CPE in the absence of ATA. Treatment with ATA during the HSV-1 infection step (ATA at Step 1) showed increased d27-1 titers in V27 cells supernatants harvested at 72 hpi (FIG. 4B). The optimal ATA concentration when added during the infection step (ATA I) was 50 μM and this was further diluted to the final concentration (f.c.) of 20 μM ATA during the dilution step by adding the remaining ⅗ vol of the media. In this case, ATA increased d27-1 titers in supernatant at the time of harvest (72 h.p.i.) about 10 times: from $4.0\pm0.3\times10^7$DRP/ml or $1.4\pm0.2\times10^7$PFU/ml to $3.7\pm0.2\times10^8$DRP/ml or $1.2\pm0.3\times10^8$PFU/ml (FIG. 4B).

In order to determine which concentrations and conditions for ATA addition have impact on HSV yields, the following experiments were conducted. ATA at varying concentrations was added to V27 cultures infected with the HSV-1 d27-1 vectors in either six-well plates (FIG. 2B) or T150 flasks (FIG. 2C) in two steps as follows. In Step 1 of the protocol, V27 cells were infected with 0.15 MOI of the rHSV vector in ⅖ of the final volume of DMEM with 10% FBS and 0-60 μM ATA concentrations. Cells were cultured for 1-2 hours at 37° C. to complete Step 1. In Step 2, the concentration of ATA was reduced to a range between 12-24 μM by the addition of ⅗ of final media volume. Cells were cultured for 70-74 hours at 37° C. and the supernatant harvested. Viral titers were expressed as Dnase Resistant Particles (DRP/ml) or Plaque Forming Units (pfu/ml) per ml and were determined as described above.

Figure 2B:
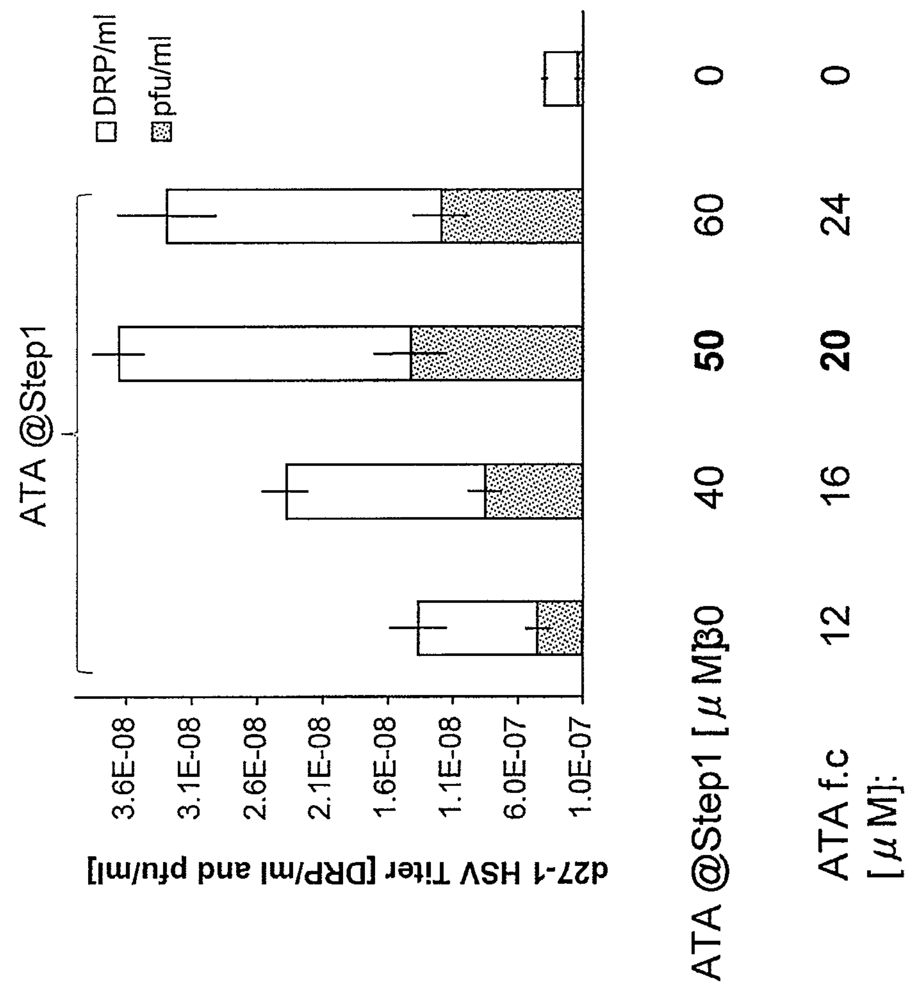
Figure 2C:
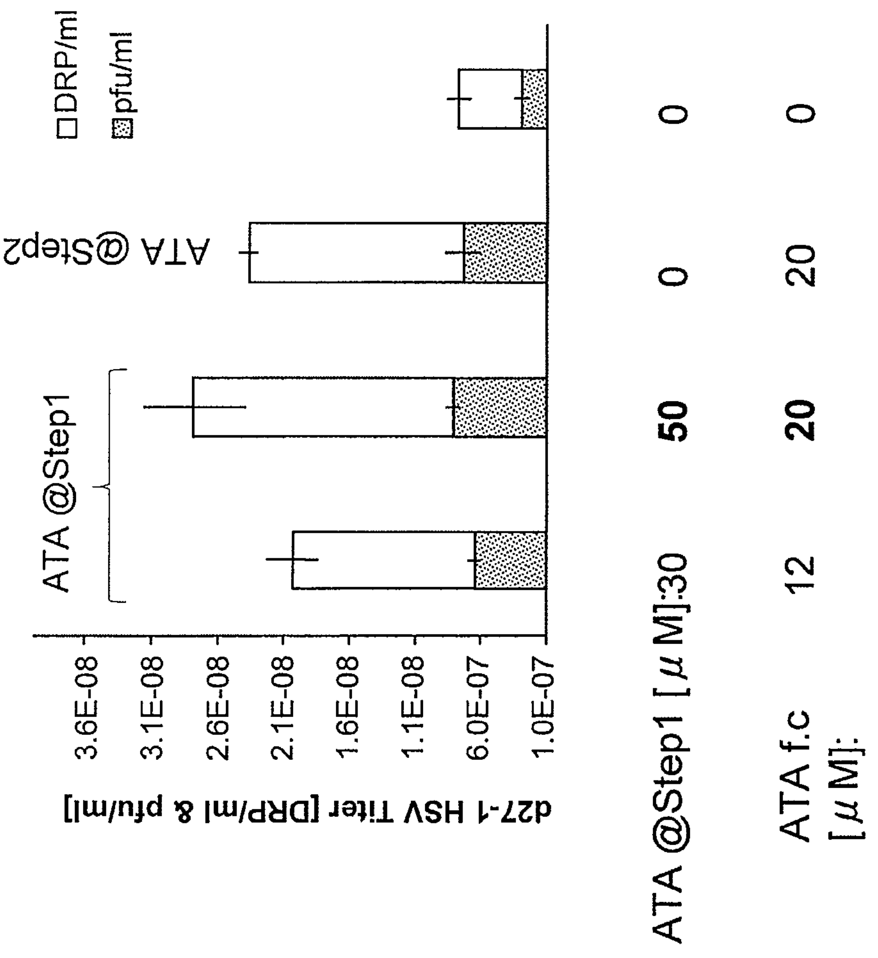

Results are shown in both FIGS. 2B and 2C and optimal ATA concentrations are bolded. As can be seen, in both six-well plates (FIG. 2B) and T150 flasks (FIG. 2C), cultures with ATA added in either of Step 1 or Step 2 had significantly higher HSV titers than those without ATA. Moreover, the highest titers were seen at ATA concentrations of 50 μM in Step 1, reduced to 20 μM in Step 2 (FIG. 2B), although all concentrations of ATA produced higher viral titers than those cultures that lacked ATA.

Figure 3:
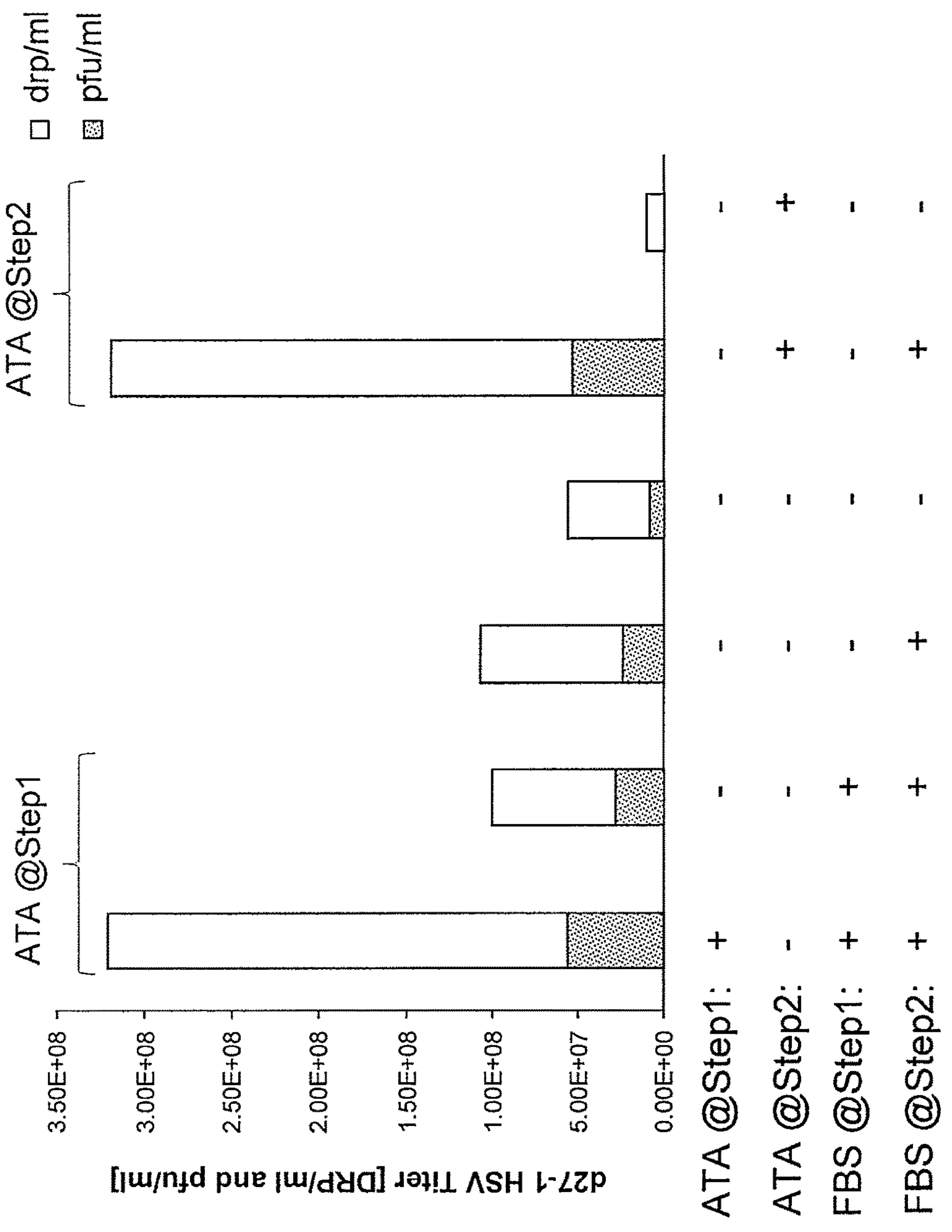
FIG. 3 shows the importance of serum presence in ATA-HSV protocol. Additional optimization and the importance of FBS presence in ATA-HSV protocol was shown on d27-1 HSV-1 titers expressed as drp/ml and pfu/ml.

Additional experiments were conducted to determine optimal conditions and the effect of the presence or absence of FBS on HSV titer. The serum presence, specifically, 10% fetal bovine serum (FBS), in ATA-containing media was the most important parameter for the ATA-induced HSV-1 titer yield. A supplementation of ATA into serum-free media during the dilution step (ATA at Step 2) caused reduction of virus titer, where the "DRP" titer was reduced below control level and PFU/ml titer was below detection (FIG. 3). An even more dramatic effect in serum-free media was seen when ATA, starting at 3 μM concentration, was supplemented during the infection Step 1 and both DRP/ml and PFU/ml titers were below the detection limit.

In this experiment, V27 cells were seeded into six well plates the day prior to infection at $6\times10^5$ cells/well. HSV 2× infection solution was prepared as follows: HSV-1 d27.1 stock was added to DMEM (no FBS) at 2× titer that the cells would be infected at final MOI 0.15. Several 2×ATA solution combinations were prepared containing either 100 μM or 40 μM ATA in DMEM and without FBS or with 20% FBS.

HSV 2× infection solution was mixed equal volumes of either DMEM−/+20% FBS or desired 2×ATA solution−/+20% FBS, vortexed, and 1 ml of infectious inoculum per well was added in Step 1. If wells contained ATA in Step 1, the concentration was 50 μM and all wells were incubated for 1-2 hrs. In Step 2, additional 1.5 ml of DMEM combinations−/+40 μM ATA and −/+20% FBS were added. If wells contained ATA whether in Step 1 or Step 2, the final ATA concentration was 20 μM. The plates were returned to the incubator for 70-74 hours after which time free media was harvested, vortexed, and centrifuged at 1,100×g for 10 minutes at 4° C. Supernatants were transferred to a new dispensing tube, vortexed, aliquoted and stocks were frozen at −80° C.

Example 3

Importance of Serum Presence in ATA-HSV Protocol

Additional experiments were conducted to determine optimal conditions and the effect of the presence or absence of FBS on HSV titer. The serum presence, specifically, 10% fetal bovine serum (FBS), in ATA-containing media was the most important parameter for the ATA-induced HSV-1 titer yield. A supplementation of ATA into serum-free media during the dilution step (ATA at Step 2) caused reduction of virus titer, where the "DRP" titer was reduced below control level and PFU/ml titer was below detection (FIG. 3). An even more dramatic effect in serum-free media was seen when ATA, starting at 3 μM concentration, was supplemented during the infection Step 1 (data not shown) and both DRP/ml and PFU/ml titers were below the detection limit.

In this experiment, V27 cells were seeded into six well plates the day prior to infection at $6\times10^5$ cells/well. HSV 2× infection solution was prepared as follows: HSV-1 d27.1 stock was added to DMEM (no FBS) at 2× titer that the cells would be infected at final MOI 0.15. Several 2×ATA solution combinations were prepared containing either 100 μM or 40 μM ATA in DMEM and without FBS or with 20% FBS. HSV 2× infection solution was mixed equal volumes of either DMEM−/+20% FBS or desired 2×ATA solution−/+20% FBS, vortexed, and 1 ml of infectious inoculum per well was added in Step 1. If wells contained ATA in Step 1, the concentration was 50 μM and all wells were incubated for 1-2 hrs. In Step 2, additional 1.5 ml of DMEM combinations−/+40 uM ATA and −/+20% FBS were added. If wells contained ATA whether in Step 1 or Step 2, the final ATA concentration was 20 μM. The plates were returned to the incubator for 70-74 hours after which time free media was harvested, vortexed, and centrifuged at 1,100×g for 10 minutes at 4° C. Supernatants were transferred to a new dispensing tube, vortexed, aliquoted and stocks were frozen at −80° C.

Example 4

Effect of ATA on Wild Type HSV Titers in Culture

Figure 4A:
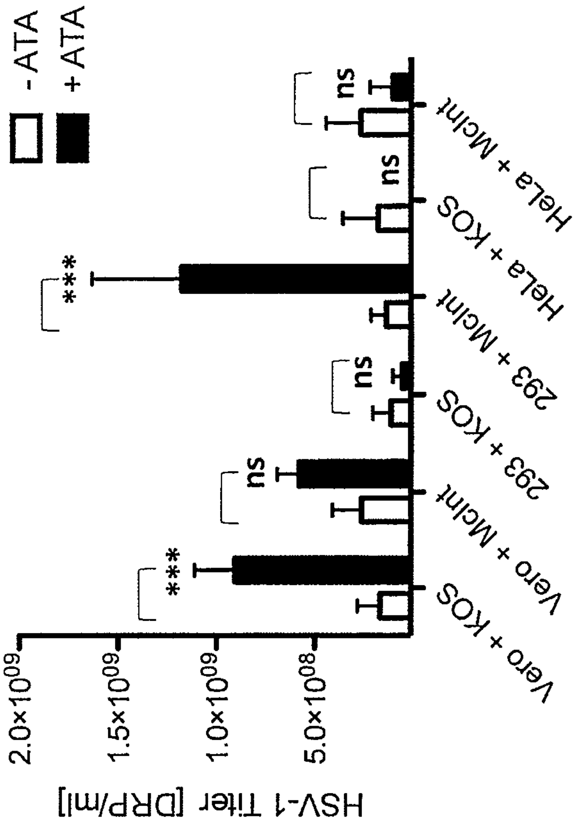
FIGS. 4A-4B show the effect of ATA on wild type HSV KOS and McIntyre strains in culture. ATA increased the yield of both virus types in Vero cells, however, ATA appeared to inhibit HSV-1 KOS growth in 293 cells. On the other hand, wtHSV-1 McIntyre strain reached the highest titers after ATA induction in 293 cells. Moreover, ATA appeared to inhibit BOTH types of HSV-1 viruses in HeLa cells.
Figure 4B:
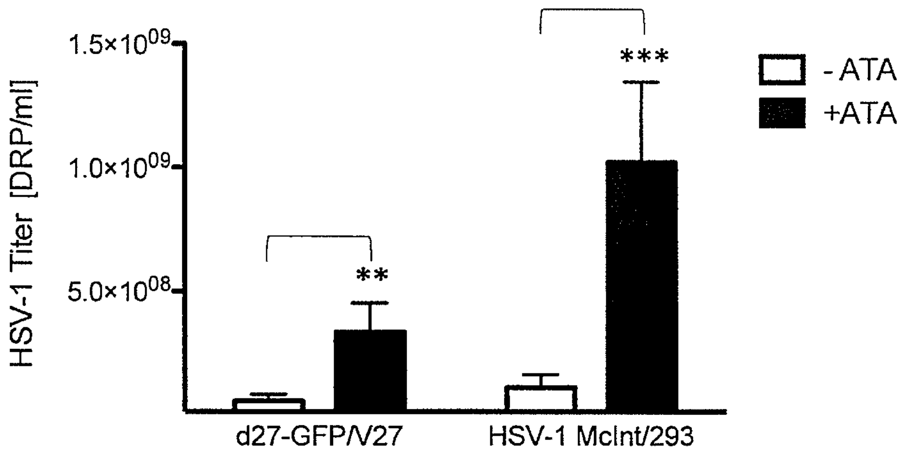

FIG. 4A shows supernatant titers of both wtHSV-1 strains, KOS and McIntyre in cell lines permissive for wtHSV-1 propagation: 293 cells, HeLa and Vero cells. wtHSV-1 strains KOS and McIntyre were propagated in 293, HeLa and Vero cells using the ATA-HSV Protocol where 50 μM ATA was added at Step 1 and the final concentration after Step 2 was diluted to 20 μM ATA. Supernatants containing virus were harvested after three days as described above. ATA increased the yield of both virus types in Vero cells. wtHSV-1 McIntyre strain reached the highest titers after ATA induction in 293 cells, however, ATA appeared to inhibit HSV-1 KOS growth in 293 cells. Finally, ATA also appeared to inhibit both types of HSV-1 viruses in HeLa cells. Two-way ANOVA; Bonferroni test; −ATA vs. +ATA: ***: $p<0.001$, ns: $p>0.05$; n=4 independent experiments.

For statistical calculations, a larger study with a set of ten independent experiments (n=10) was conducted in 6-well plates with or without ATA added during the infection step (Step 1) comparing replication-deficient d27-GFP and also wtHSV-1 McIntyre strain in order to investigate, whether ATA could increase the titer in the wtHSV-1 strain as well (FIG. 4B). ATA was added at 50 mM to confluent cell monolayers, V27 cells for d27-1 or 293 cells for wtHSV-1 McIntyre, during the infection step (Step 1) and the cells were infected with vectors at MOI=0.15 while ATA was diluted 1 hr later to a final 20 mM concentration. After ATA addition, d27-1 titer significantly increased 6.1 times from $5.4\times10^7$DRP/ml or $1.1\times10^8$DRP/ml ($P<0.01$) and wtHSV-1 McIntyre significantly increased 9.1 times from $3.3\times10^8$DRP/ml or $1.0\times10^9$ DRP/ml (*$P<0.001$) as analyzed by 2-way ANOVA and Bonferroni test (FIG. 4B).

Example 5

Effect of ATA in HSV Stocks on the Production or rAAV Virions

Figure 5A:
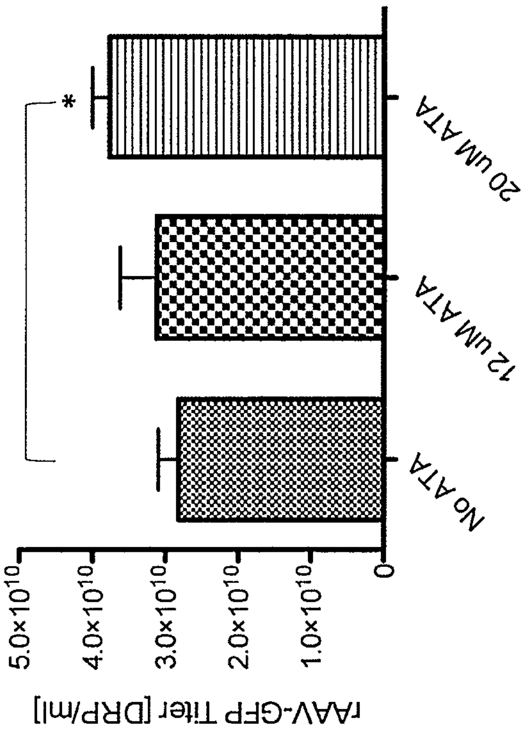
FIGS. 5A-5B show the effect of ATA in HSV stocks on the production of rAAV Virions. rAAV titers were slightly increased when using the HSV stock prepared with 20 μM ATA added during infection. ATA was also shown to increase rAAV titer when 10 μM ATA was spiked directly into 293 cell media during 2 hrs of the HSV coinfection step.

In order to determine whether the presence of ATA during HSV production impacted the yield of rAAV virions produced using HSV vectors, the following experiment was performed showing rAAV titers affected by ATA residue present from rHSV-1 stocks produced in 293 cells (FIG. 5A). The rAAV-GFP vector was produced by co-infection ofrHSV-rep2/cap2 and rHSV-EGFP vectors in 293 cells 60 mm plates using ATA-containing rHSV-lstocks prepared under different concentrations ATA concentrations (12 μM or 20 μM f.c.) (see Material and Methods). rAAV DRP/ml titer was slightly increased by 1.3 times when using the rHSV-rep2/cap2 stock that was prepared with 20 μM ATA added during infection (ATA Step 1) versus "No ATA" Control (*p<0.05), where the ATA concentration during rAAV production was approximately 3 μM. No significant rAAV titer increase was detected when using the rHSV-rep2/cap2 stock that was prepared with 12 μM ATA (FIG. 5A). One-way ANOVA; Tukey's-test:*p<0.05; 20 μM ATA vs. No ATA; n=4 independent experiments.

Figure 5B:
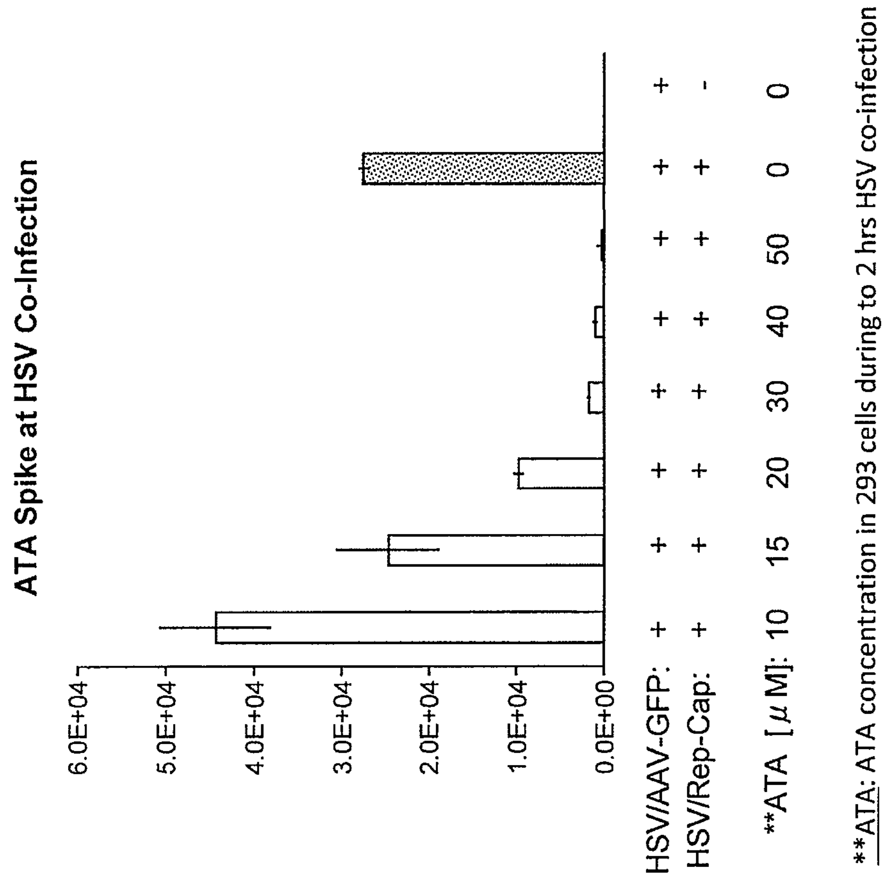

In another experiment, ATA was shown to increase rAAV titer when 10 μM ATA was spiked directly into 293 cells media during 2 hrs of rHSV-rep2/cap2 and rHSV-EGFP co-infection step. This effect was not observed when the ATA concentrations were higher then 20 μM (FIG. 5B).

Example 6

ATA Mechanism of Action

In order to illuminate the ATA mechanism of action by human genome array and the fact that Vero and V27 are monkey-derived cell lines, wtHSV-1 propagation was tested in several human cell lines (FIGS. 4A-4B). A propagation of two wild type HSV-1 (wtHSV-1) strains, KOS and McIntyre, were compared in three cell lines: human embryonic kidney 293 (293 cells), human cervical cancer HeLa cells and African green monkey kidney epithelial Vero cells. The experiments were carried out in 10% FBS-containing media following the ATA I protocol scheme, where 50 μM ATA was supplemented during the infection step and further diluted to 20 μM ATA concentration (see Material and Methods). In human-derived 293 cells, only the wtHSV-1 McIntyre virus titer increased significantly by ATA, from $1.4\times10^8$DRP/ml to $1.2\times10^9$DRP/ml (*p<0.001). In Vero cells, ATA significantly increased titers only in wtHSV-1 KOS strain from $1.7\times10^8$DRP/ml up to $9.1\times10^8$DRP/ml (*p<0.001; both statistics: Two-way ANOVA, Bonferroni test; n=4). Surprisingly, in HeLa cells, ATA seemed to inhibit propagation of both KOS and McIntyre HSV-1 strains.

To identify cell response gene signatures to wtHSV-1 McIntyre infection, transcriptional profiling was done using Affymetrix Human U133 Plus 2.0 Array with 293 cells that were either mock-treated, ATA-treated (ATA), wtHSV-1 McIntyre-infected (HSV) or ATA-treated and wtHSV-1 McIntyre-infected (HSV&ATA) for 24 h. Gene expression changes induced by infection or ATA treatment were identified by referencing the gene expression level for each probe to that corresponding in the uninfected cells sample. HSV-1 infection alone had strong impact on the gene expression profile of 293 cells when compared to untreated cells gene profile.

First, a filtering step was applied to filter out low expression and out of 54,675 total Affy U133 Plus2 probes, 41,569 (76%) probes remained after the cutoff. Principle Component Analysis revealed two distinct populations, samples treated with and without HSV. ANOVA was performed to find significant differential transcripts between HSV versus Vehicle, ATA versus Vehicle, HSV+AVA versus Vehicle, and HSV+ATA versus HSV alone. Significant genes were considered less than a p-value of 0.01. A self-organized map was used to examine patterns of expression among Vehicle, HSV1, and HSV1+ATA. A distinct cluster of genes was found, Cluster A and B (Tables 1 and 2), that showed changes in transcriptional profiles caused by HSV-1 and their correction by ATA that brought these genes back to vehicle baseline.

The biological functions of these clusters were analyzed in GeneGo. Cluster A (Table 2) represented 58 probes that showed up-regulation in HSV-1 and suppression after the addition of ATA. These genes were primarily involved in inflammatory IgE and IFN signaling, and general immune response. Cluster B (Table 1) represented 152 probes that showed down-regulation by HSV-1 and their subsequent ATA up-regulation by bringing them back to vehicle baseline. Genes in this cluster were primarily involved in cell cycle G1/S, signal transduction in PTEN, and WNT development. For example, ATA in the presence of HSV-1 up-regulated CDC25A, CDKN1A, CDKNIC, CCNK, CNNM2 genes from cell cycle progression pathways and genes from Ras/Raf/MEK pathway, such as FOXC1, FOXD3, FOXO3 (See, Table 1).

Tables 3A and 3B show nNOS, iNOS and eNOS expression reduction in HSV ATA samples as analyzed by Affymetrix Gen Array and iNOS expression reduction in HSV+ATA samples as analyzed by Qiagene SAB Jak-Stat RT-PCR Microarray

Example 7

Effect of Dexamethasone on HSV Yields

Figure 6:
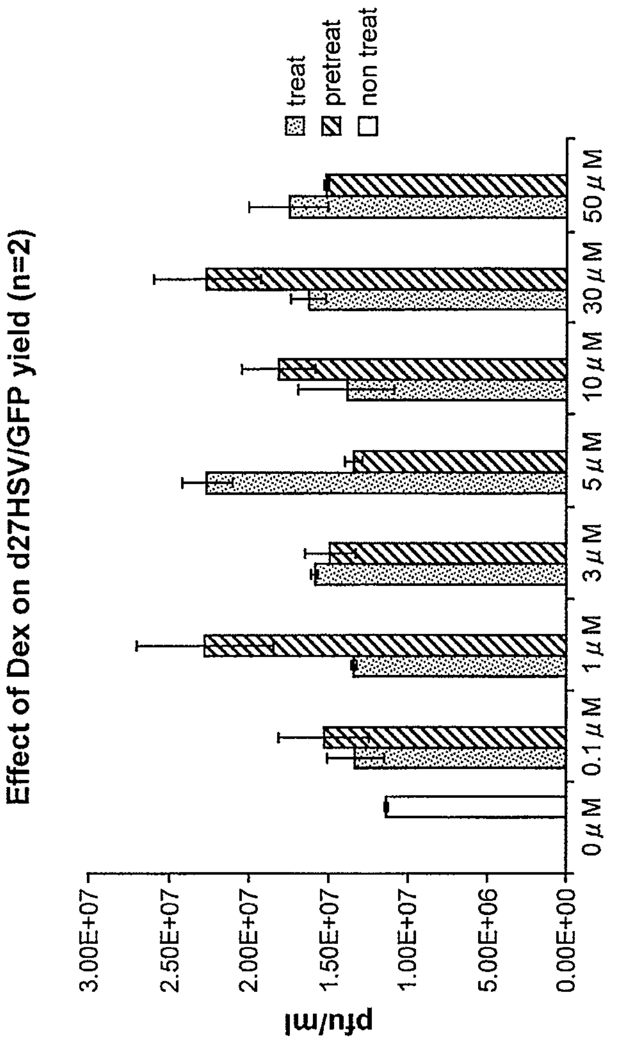
FIG. 6 shows the effect of dexamethasone (Dex) on d27-1/GFP HSV-1 viral titer. The final titers d27-1/GFP HSV-1 were, in general, slightly elevated after dex pretreatments or treatments as compared to untreated control.

In order to determine whether the iNOS inhibitor dexamethasone also increased rHSV yields in culture, the following experiment was conducted (FIG. 6). shows the effect of dexamethasone (Dex) on d27-1/GFP HSV-1 viral titer. The final titers d27-1/GFP HSV-1 were, in general, slightly elevated after dex pretreatments or treatments as compared to untreated control.

V27 cells were seeded into six well plates the day prior to infection at $6\times10^5$ cells/well and the next day, different concentrations of dexamethasone (dex) were added to the wells either before HSV-1 infection (pretreat) or during the infection (treat) in ⅖ vol of DMEM-10% FBS media. After 1-2 hours of incubation at 37° C., ⅗ vol. of DMEM-10% FBS was added. The cultures were returned to the incubator and supernatant was harvested after 70-74 hours. The data are shown as Mean value of titers±S.D. in pfu/ml (n=2).

Example 8

Effect of Valproic Acid on HSV Yields

Figure 7:
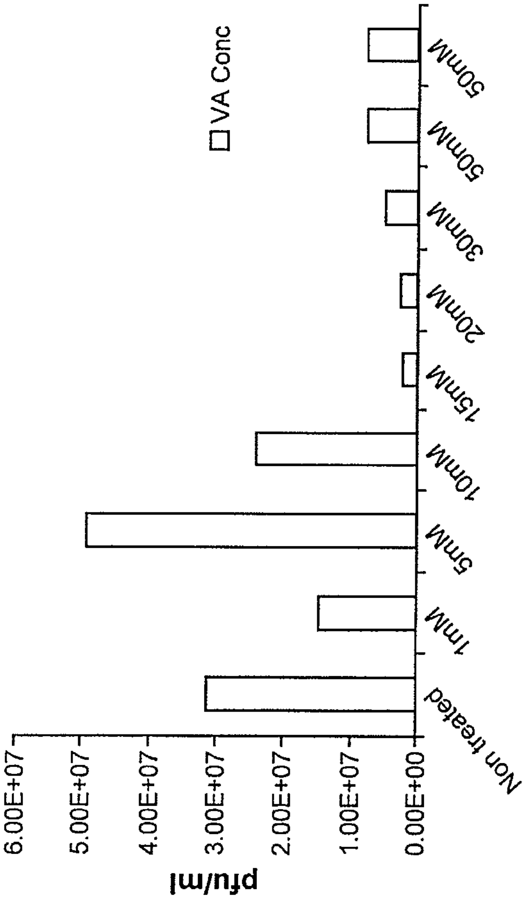
FIG. 7 shows the effect of pretreatment by valproic acid (VA) on d27-1/GFP HSV-1 viral titer. VA at a concentration 5 mM slightly elevated the titer of d27-1/GFP HSV-1, however the concentrations bellow and above of 5 mM appeared to have an inhibitory effect on d27-1/GFP HSV-1 titer, as compared to untreated control.

In order to determine whether the iNOS inhibitor valproic acid also increased rHSV yields in culture, the following experiment was conducted. FIG. 7 shows the effect of pretreatment by valproic acid (VA) on d27-1/GFP HSV-1 viral titer. VA at concentration 5 mM slightly elevated the titer of d27-1/GFP HSV-1, however the concentrations bellow and above of 5 mM appear to have an inhibitory effect on d27-1/GFP HSV-1 titer, as compared to untreated control.

V27 cells were seeded into six well plates the day prior to infection at $6\times10^5$ cells/well and the next day, different concentrations of VA were added to wells. Plates were incubated for 6 hrs, aspirated and ⅖ vol of media containing infectious HSV-1 d27-1 stock was added and incubated for 1-2 hours at 37° C., 5 after which time ⅗ vol of DMEM 10% FBS media was added. The cultures were returned to the incubator and supernatant was harvested after 70-74 hours.

As shown in the foregoing examples, ATA in micromolar concentrations increases HSV-1 vector yield. This finding is important for both large-scale HSV production, as well as rHSV and rAAV vector production. Moreover and surprisingly, the presence of ATA in rHSV-1 stocks did not negatively influence rAAV yield. This result is surprising as ATA in millimolar amounts and higher concentrations is known to be an antiviral agent (Cushman et al., *J. Med. Chem.* (1991) 34:329-337; Zhang et al., Antiviral Res. (1999) 43:23-35; Yap et al., *Computational Biol. and Chem.* (2005) 29:212-219; De Clercq, *Advents, Advances, and Adventures Med. Res. Rev.* (2011) 31:118-160). In serum-free media the inventors have also observed a possible antiviral effect of ATA at micromolar concentrations, but not in the presence of serum (10% FBS).

Also as shown herein, ATA treatment delayed HSV-1 plaque formation and cell lysis in V27 cells monolayers and cytopathic effect (CPE), which evidences antiapoptotic properties. The mechanism of action of ATA in the increase of HSV-1 yield appears to involve changes in factors required for HSV-1 production and reduction of cellular innate antiviral immune response responsible for a viral clearance. From the Human Genome Array analysis above, it was discovered that HSV-1 infection alone has strong impact on the gene expression profile of 293 cells and the effect of ATA was mostly observed in cells treated with both HSV-1 and ATA. Genes involved in cell cycle G1/S, signal transduction in PTEN, and WNT development were significantly down-regulated by HSV-1 and up-regulated after addition of ATA.

Genes primarily involved in inflammatory IgE and IFN signaling, and general immune response were up-regulated by HSV-1 and suppressed after the addition of ATA. In the presence of HSV-1, ATA up-regulated CDC25A, CDKN1A, CDKN1C, CCNK, CNNM2 genes from the cell cycle progression pathways and genes from the Ras/Raf/MEK pathway, including FOXC1, FOXD3, FOXO3.

The finding that ATA can increase HSV-1 yield are important because of the need of higher yields of HSV-1 vectors for large-scale production for gene therapy and other applications.

Thus, methods for increasing viral yields using iNOS inhibitors are described. Although preferred embodiments of the subject invention have been described in some detail, it is understood that obvious variations can be made without departing from the spirit and the scope of the invention as defined herein.

TABLE 1

Cluster B gene list: Genes suppressed by HSV and up-regulated by HSV + ATA

| Probe_Set_ID | Gene Symbol | Gene_Title | Estimate of HSV + ATA vs HSV | p-Value for Estimate of HSV + ATA vs HSV |
|---|---|---|---|---|
| 230304_at | — | — | 2.1691 | 0.0001 |
| 225806_at | JUB | jub, ajuba homolog (*Xenopus laevis*) | 2.126171 | 0.0004 |
| 202935_s_at | SOX9 | SRY (sex determining region Y)-box 9 | 1.855105 | 0.000046 |
| 204790_at | SMAD7 | SMAD family member 7 | 1.797951 | 0.0029 |
| 214633_at | SOX3 | SRY (sex determining region Y)-box 3 | 1.797254 | 0.000007 |
| 210512_s_at | VEGFA | vascular endothelial growth factor A | 1.754719 | 0.000021 |
| 216652_s_at | DR1 | down-regulator of transcription 1, TBP-binding (negative cofactor 2) | 1.74529 | 0.0036 |
| 205932_s_at | MSX1 | msh homeobox 1 | 1.726634 | 6.90E−06 |
| 209348_s_at | MAF | v-maf musculoaponeurotic fibrosarcoma oncogene homolog (avian) | 1.685705 | 0.0073 |
| 217028_at | CXCR4 | chemokine (C-X-C motif) receptor 4 | 1.652962 | 0.0093 |
| 218251_at | MID1IP1 | MID1 interacting protein 1 (gastrulation specific G12 homolog (zebrafish)) | 1.642017 | 0.0064 |
| 1553764_a_at | JUB | jub, ajuba homolog (*Xenopus laevis*) | 1.623019 | 0.0017 |
| 214446_at | ELL2 | elongation factor, RNA polymerase II, 2 | 1.602283 | 0.0001 |
| 227718_at | PURB | purine-rich element binding protein B | 1.59314 | 0.0019 |
| 219624_at | BAG4 | BCL2-associated athanogene 4 | 1.578527 | 0.0007 |
| 225642_at | KTI12 | KTI12 homolog, chromatin associated (*S. cerevisiae*) | 1.566082 | 0.0002 |
| 203705_s_at | FZD7 | frizzled homolog 7 (*Drosophila*) | 1.54382 | 0.0002 |
| 222696_at | AXIN2 | axin 2 | 1.526076 | 0.0066 |
| 202007_at | NID1 | nidogen 1 | 1.521713 | 0.0029 |
| 226858_at | CSNK1E | casein kinase 1, epsilon | 1.51752 | 0.0002 |
| 57739_at | DND1 | dead end homolog 1 (zebrafish) | 1.515518 | 0.0005 |
| 1558290_a_at | PVT1 | Pvt1 oncogene (non-protein coding) | 1.515288 | 0.0016 |

TABLE 1-continued

| Probe_Set_ID | Gene Symbol | Gene_Title | Estimate of HSV + ATA vs HSV | p-Value for Estimate of HSV + ATA vs HSV |
|---|---|---|---|---|
| Cluster B gene list: Genes suppressed by HSV and up-regulated by HSV + ATA | | | | |
| 215694_at | SPATA5L1 | spermatogenesis associated 5-like 1 | 1.51283 | 0.0012 |
| 206302_s_at | NUDT4 /// NUDT4P1 | nudix (nucleoside diphosphate linked moiety X)-type motif 4 /// nudix (nucleoside diphosphate linked moiety X)-type motif 4 pseudogene 1 | 1.49443 | 0.0073 |
| 218486_at | KLF11 | Kruppel-like factor 11 | 1.493386 | 0.0006 |
| 201695_s_at | NP | nucleoside phosphorylase | 1.492386 | 0.0004 |
| 203002_at | AMOTL2 | angiomotin like 2 | 1.489062 | 0.0093 |
| 227195_at | ZNF503 | zinc finger protein 503 | 1.478008 | 0.0094 |
| 238012_at | DPP7 | Dipeptidyl-peptidase 7 | 1.471194 | 0.0003 |
| 209905_at | HOXA9 | homeobox A9 | 1.46661 | 0.0003 |
| 209188_x_at | DR1 | down-regulator of transcription 1, TBP-binding (negative cofactor 2) | 1.4541 | 0.0001 |
| 221168_at | PRDM13 | PR domain containing 13 | 1.448075 | 0.0043 |
| 213338_at | TMEM158 | transmembrane protein 158 | 1.436626 | 0.0001 |
| 209098_s_at | JAG1 | jagged 1 (Alagille syndrome) | 1.433177 | 0.0001 |
| 206300_s_at | PTHLH | parathyroid hormone-like hormone | 1.430301 | 0.0004 |
| 220018_at | CBLL1 | Cas-Br-M (murine) ecotropic retroviral transforming sequence-like 1 | 1.427214 | 0.00003 |
| 226284_at | ZBTB2 | zinc finger and BTB domain containing 2 | 1.421748 | 6.50E−06 |
| 213348_at | CDKN1C | cyclin-dependent kinase inhibitor 1C (p57, Kip2) | 1.413731 | 0.0001 |
| 209565_at | RNF113A | ring finger protein 113A | 1.413412 | 7.80E−06 |
| 239696_at | — | — | 1.413287 | 0.0006 |
| 212696_s_at | RNF4 | ring finger protein 4 | 1.408882 | 0.0034 |
| 214651_s_at | HOXA9 | homeobox A9 | 1.404355 | 0.000042 |
| 217741_s_at | ZFAND5 | zinc finger, AN1-type domain 5 | 1.401465 | 0.0003 |
| 229309_at | ADRB1 | adrenergic, beta-1-, receptor | 1.398788 | 0.0008 |
| 228953_at | WHAMM | WAS protein homolog associated with actin, golgi membranes and microtubules | 1.392654 | 0.0013 |
| 1554522_at | CNNM2 | cyclin M2 | 1.389108 | 0.0049 |
| 204913_s_at | SOX11 | SRY (sex determining region Y)-box 11 | 1.385923 | 0.0004 |
| 231901_at | C19orf52 | chromosome 19 open reading frame 52 | 1.378798 | 0.0034 |
| 224314_s_at | EGLN1 | egl nine homolog 1 (*C. elegans*) | 1.375757 | 0.0001 |
| 209099_x_at | JAG1 | jagged 1 (Alagille syndrome) | 1.374203 | 0.0029 |
| 205555_s_at | MSX2 | msh homeobox 2 | 1.368114 | 0.00003 |
| 216035_x_at | TCF7L2 | transcription factor 7-like 2 (T-cell specific, HMG-box) | 1.368112 | 0.0003 |
| 225824_at | CCNK | cyclin K | 1.363977 | 0.0076 |
| 209201_x_at | CXCR4 | chemokine (C-X-C motif) receptor 4 | 1.360311 | 0.0001 |
| 235147_at | FLJ32063 | Hypothetical LOC150538 | 1.357503 | 0.0008 |
| 204527_at | MYO5A | myosin VA (heavy chain 12, myoxin) | 1.356721 | 0.0017 |
| 242963_at | SGMS2 | sphingomyelin synthase 2 | 1.356199 | 0.0008 |
| 218247_s_at | MEX3C | mex-3 homolog C (*C. elegans*) | 1.3496 | 0.0001 |
| 207654_x_at | DR1 | down-regulator of transcription 1, TBP- | 1.348295 | 9.30E−06 |

TABLE 1-continued

Cluster B gene list: Genes suppressed by HSV and up-regulated by HSV + ATA

| Probe_Set_ID | Gene Symbol | Gene_Title | Estimate of HSV + ATA vs HSV | p-Value for Estimate of HSV + ATA vs HSV |
|---|---|---|---|---|
| | | binding (negative cofactor 2) | | |
| 209357_at | CITED2 | Cbp/p300-interacting transactivator, with Glu/Asp-rich carboxy-terminal domain, 2 | 1.347165 | 0.0002 |
| 202241_at | TRIB1 | tribbles homolog 1 (*Drosophila*) | 1.340674 | 0.0009 |
| 209372_x_at | TUBB2A /// TUBB2B | tubulin, beta 2A /// tubulin, beta 2B | 1.339095 | 0.0001 |
| 205541_s_at | GSPT2 | G1 to S phase transition 2 | 1.33517 | 0.005 |
| 1568815_a_at | DDX50 | DEAD (Asp-Glu-Ala-Asp) box polypeptide 50 | 1.329483 | 0.0043 |
| 204805_s_at | H1FX | H1 histone family, member X | 1.324347 | 0.0013 |
| 213152_s_at | SFRS2B | splicing factor, arginine/serine-rich 2B | 1.322967 | 6.70E−06 |
| 225699_at | C7orf40 | chromosome 7 open reading frame 40 | 1.321373 | 0.0014 |
| 218295_s_at | NUP50 | nucleoporin 50 kDa | 1.318229 | 0.0014 |
| 224739_at | PIM3 | pim-3 oncogene | 1.31654 | 0.0001 |
| 214911_s_at | BRD2 | bromodomain containing 2 | 1.313049 | 0.0015 |
| 208938_at | PRCC | papillary renal cell carcinoma (translocation-associated) | 1.304724 | 0.000041 |
| 206907_at | TNFSF9 | tumor necrosis factor (ligand) superfamily, member 9 | 1.295621 | 0.0032 |
| 202284_s_at | CDKN1A | cyclin-dependent kinase inhibitor 1A (p21, Cip1) | 1.28534 | 0.0001 |
| 206915_at | NKX2-2 | NK2 homeobox 2 | 1.280773 | 0.000021 |
| 215087_at | C15orf39 | chromosome 15 open reading frame 39 | 1.277596 | 0.0013 |
| 202219_at | SLC6A8 | solute carrier family 6 (neurotransmitter transporter, creatine), member 8 | 1.273131 | 0.0006 |
| 202704_at | TOB1 | transducer of ERBB2, 1 | 1.272848 | 0.0016 |
| 213038_at | RNF19B | ring finger protein 19B | 1.27284 | 0.0022 |
| 213150_at | HOXA10 | homeobox A10 | 1.272477 | 0.008 |
| 204383_at | DGCR14 | DiGeorge syndrome critical region gene 14 | 1.268562 | 0.000043 |
| 1553613_s_at | FOXC1 | forkhead box C1 | 1.26852 | 0.0003 |
| 218398_at | MRPS30 | mitochondrial ribosomal protein S30 | 1.266043 | 0.0057 |
| 202166_s_at | PPP1R2 | protein phosphatase 1, regulatory (inhibitor) subunit 2 | 1.264115 | 0.00003 |
| 235004_at | RBM24 | RNA binding motif protein 24 | 1.260011 | 0.0086 |
| 223742_at | MRPL4 | mitochondrial ribosomal protein L4 | 1.251284 | 0.000049 |
| 211756_at | PTHLH | parathyroid hormone-like hormone | 1.24883 | 0.0016 |
| 209211_at | KLF5 | Kruppel-like factor 5 (intestinal) | 1.241821 | 0.0003 |
| 225796_at | PXK | PX domain containing serine/threonine kinase | 1.239504 | 0.0002 |
| 225434_at | DEDD2 | death effector domain containing 2 | 1.23754 | 0.000044 |
| 208686_s_at | BRD2 | bromodomain containing 2 | 1.229145 | 0.0001 |
| 217821_s_at | WBP11 | WW domain binding protein 11 | 1.218077 | 0.0002 |
| 244519_at | ASXL1 | additional sex combs like 1 (*Drosophila*) | 1.208056 | 0.000044 |
| 208415_x_at | ING1 | inhibitor of growth family, member 1 | 1.184054 | 0.0017 |

TABLE 1-continued

| Probe_Set_ID | Gene Symbol | Gene_Title | Estimate of HSV + ATA vs HSV | p-Value for Estimate of HSV + ATA vs HSV |
|---|---|---|---|---|
| Cluster B gene list: Genes suppressed by HSV and up-regulated by HSV + ATA | | | | |
| 216511_s_at | TCF7L2 | transcription factor 7-like 2 (T-cell specific, HMG-box) | 1.174677 | 0.0024 |
| 235959_at | — | — | 1.172362 | 0.0008 |
| 243707_at | — | — | 1.171741 | 0.0005 |
| 227852_at | RP9 | retinitis pigmentosa 9 (autosomal dominant) | 1.171328 | 0.0002 |
| 1555772_a_at | CDC25A | cell division cycle 25 homolog A (*S. pombe*) | 1.170244 | 0.0051 |
| 221841_s_at | KLF4 | Kruppel-like factor 4 (gut) | 1.16333 | 0.0006 |
| 214789_x_at | SFRS2B | splicing factor, arginine/serine-rich 2B | 1.162135 | 0.0001 |
| 216997_x_at | TLE4 | transducin-like enhancer of split 4 (E(sp1) homolog, *Drosophila*) | 1.159916 | 0.0001 |
| 205780_at | BIK | BCL2-interacting killer (apoptosis-inducing) | 1.158085 | 0.0001 |
| 212075_s_at | CSNK2A1 | casein kinase 2, alpha 1 polypeptide | 1.156022 | 0.0049 |
| 228820_at | XPNPEP3 | X-prolyl aminopeptidase (aminopeptidase P) 3, putative | 1.152448 | 0.0008 |
| 209653_at | KPNA4 | karyopherin alpha 4 (importin alpha 3) | 1.146903 | 0.0004 |
| 209457_at | DUSP5 | dual specificity phosphatase 5 | 1.144663 | 0.0016 |
| 224671_at | MRPL10 | mitochondrial ribosomal protein L10 | 1.144585 | 0.0061 |
| 200618_at | LASP1 | LIM and SH3 protein 1 | 1.140405 | 0.0097 |
| 228931_at | COQ4 | coenzyme Q4 homolog (*S. cerevisiae*) | 1.136018 | 0.0008 |
| 224583_at | COTL1 | coactosin-like 1 (Dictyostelium) | 1.128103 | 0.001 |
| 238738_at | PSMD7 | Proteasome (prosome, macropain) 26S subunit, non-ATPase, 7 | 1.128031 | 0.0062 |
| 202501_at | MAPRE2 | microtubule-associated protein, RP/EB family, member 2 | 1.12791 | 0.0046 |
| 214321_at | NOV | nephroblastoma overexpressed gene | 1.123481 | 0.0004 |
| 202936_s_at | SOX9 | SRY (sex determining region Y)-box 9 | 1.12181 | 0.0054 |
| 222163_s_at | SPATA5L1 | spermatogenesis associated 5-like 1 | 1.116794 | 0.0013 |
| 241612_at | FOXD3 | forkhead box D3 | 1.11263 | 0.0041 |
| 202431_s_at | MYC | v-myc myelocytomatosis viral oncogene homolog (avian) | 1.105333 | 0.0007 |
| 215933_s_at | HHEX | hematopoietically expressed homeobox | 1.105321 | 0.0002 |
| 204132_s_at | FOXO3 /// FOXO3B | forkhead box O3 /// forkhead box O3B pseudogene | 1.100606 | 0.0007 |
| 201041_s_at | DUSP1 | dual specificity phosphatase 1 | 1.09043 | 0.0004 |
| 230233_at | — | — | 1.087609 | 0.0005 |
| 215223_s_at | SOD2 | superoxide dismutase 2, mitochondrial | 1.087493 | 0.0001 |
| 225689_at | C3orf39 | chromosome 3 open reading frame 39 | 1.080337 | 0.003 |
| 223132_s_at | TRIM8 | tripartite motif-containing 8 | 1.073976 | 0.0065 |
| 203313_s_at | TGIF1 | TGFB-induced factor homeobox 1 | 1.073363 | 0.0008 |
| 201461_s_at | MAPKAPK2 | mitogen-activated protein kinase-activated protein kinase 2 | 1.070375 | 0.0088 |
| 236174_at | — | — | 1.069052 | 0.0013 |

TABLE 1-continued

| Cluster B gene list: Genes suppressed by HSV and up-regulated by HSV + ATA | | | | |
|---|---|---|---|---|
| Probe_Set_ID | Gene Symbol | Gene_Title | Estimate of HSV + ATA vs HSV | p-Value for Estimate of HSV + ATA vs HSV |
| 223679_at | CTNNB1 | catenin (cadherin-associated protein), beta 1, 88 kDa | 1.060314 | 0.0044 |
| 204039_at | CEBPA | CCAAT/enhancer binding protein (C/EBP), alpha | 1.052213 | 0.01 |
| 234302_s_at | ALKBH5 | alkB, alkylation repair homolog 5 (*E. coli*) | 1.049599 | 0.0043 |
| 223290_at | PDXP | pyridoxal (pyridoxine, vitamin B6) phosphatase | 1.048187 | 0.0022 |
| 226644_at | MIB2 | mindbomb homolog 2 (*Drosophila*) | 1.041356 | 0.0011 |
| 206363_at | MAF | v-maf musculoaponeurotic fibrosarcoma oncogene homolog (avian) | 1.037386 | 0.0008 |
| 1555639_a_at | RBM14 | RNA binding motif protein 14 | 1.035626 | 0.0003 |
| 222527_s_at | RBM22 | RNA binding motif protein 22 | 1.027056 | 0.0008 |
| 213419_at | APBB2 | amyloid beta (A4) precursor protein-binding, family B, member 2 | 1.025879 | 0.0009 |
| 213360_s_at | POM121 /// POM121C | POM121 membrane glycoprotein (rat) /// POM121 membrane glycoprotein C | 1.023715 | 0.0013 |
| 225832_s_at | DAGLB | diacylglycerol lipase, beta | 1.001586 | 0.0001 |
| 212445_s_at | NEDD4L | neural precursor cell expressed, developmentally down-regulated 4-like | 0.997235 | 0.0022 |
| 224562_at | WASF2 | WAS protein family, member 2 | 0.996687 | 0.0043 |
| 223389_s_at | ZNF581 | zinc finger protein 581 | 0.99618 | 0.0004 |
| 231721_at | JAM3 | junctional adhesion molecule 3 | 0.989941 | 0.0001 |
| 203140_at | BCL6 | B-cell CLL/lymphoma 6 | 0.984695 | 0.0004 |
| 213823_at | HOXA11 | homeobox A11 | 0.974615 | 0.0036 |
| 1552275_s_at | PXK | PX domain containing serine/threonine kinase | 0.973552 | 0.0002 |
| 52731_at | AMBRA1 | autophagy/beclin-1 regulator 1 | 0.970744 | 0.000027 |
| 238624_at | — | — | 0.970064 | 0.0005 |
| 210479_s_at | RORA | RAR-related orphan receptor A | 0.965295 | 0.0006 |
| 220941_s_at | C21orf91 | chromosome 21 open reading frame 91 | 0.943651 | 0.0013 |
| 203234_at | UPP1 | uridine phosphorylase 1 | 0.932337 | 0.0009 |
| 202102_s_at | BRD4 | bromodomain containing 4 | 0.930432 | 0.0034 |
| 217775_s_at | RDH11 | retinol dehydrogenase 11 (all-trans/9-cis/11-cis) | 0.92863 | 0.0029 |

TABLE 2

| Cluster A gene list: Genes up-regulated by HSV and down-regulated by HSV + ATA | | | | |
|---|---|---|---|---|
| Probe_Set_ID | Gene Symbol | Gene_Title | Estimate of HSV1_ATA_vs_HSV1 | p-Value for Estimate of HSV1_ATA_vs_HSV1 |
| 243160_at | — | — | −1.01645 | 0.0022 |
| 205247_at | NOTCH4 | Notch homolog 4 (*Drosophila*) | −0.93759 | 0.0007 |
| 219256_s_at | SH3TC1 | SH3 domain and | −0.91997 | 0.0021 |

TABLE 2-continued

Cluster A gene list: Genes up-regulated by HSV and down-regulated by HSV + ATA

| Probe_Set_ID | Gene Symbol | Gene_Title | Estimate of HSV1_ATA_vs_HSV1 | p-Value for Estimate of HSV1_ATA_vs_HSV1 |
|---|---|---|---|---|
| | | tetratricopeptide repeats 1 | | |
| 221631_at | CACNA1I | calcium channel, voltage-dependent, T type, alpha 1I subunit | −0.90394 | 0.0018 |
| 1569961_at | — | — | −0.89195 | 0.0013 |
| 220277_at | CXXC4 | CXXC finger 4 | −0.85343 | 0.0054 |
| 229611_at | LMLN | leishmanolysin-like (metallopeptidase M8 family) | −0.85329 | 0.0005 |
| 232341_x_at | HABP4 | hyaluronan binding protein 4 | −0.84077 | 0.0071 |
| 242219_at | — | — | −0.83521 | 0.0028 |
| 233767_at | HHLA1 | HERV-H LTR-associating 1 | −0.8339 | 0.0017 |
| 236925_at | LOC728288 | hypothetical LOC728288 | −0.81812 | 0.008 |
| 231905_at | C20orf96 | chromosome 20 open reading frame 96 | −0.80575 | 0.0041 |
| 233313_at | — | — | −0.80466 | 0.0011 |
| 1563507_at | — | — | −0.79441 | 0.0043 |
| 232456_at | C10orf71 | chromosome 10 open reading frame 71 | −0.78722 | 0.0067 |
| 203468_at | CDK10 | cyclin-dependent kinase 10 | −0.77888 | 0.0035 |
| 237456_at | — | — | −0.77558 | 0.0085 |
| 216127_at | PDIA2 | protein disulfide isomerase family A, member 2 | −0.76924 | 0.0049 |
| 207977_s_at | DPT | dermatopontin | −0.76077 | 0.0065 |
| 224510_s_at | CLPB | ClpB caseinolytic peptidase B homolog (*E. coli*) | −0.75625 | 0.006 |
| 208267_at | TRPV5 | transient receptor potential cation channel, subfamily V, member 5 | −0.73228 | 0.0091 |
| 221868_at | PAIP2B | poly(A) binding protein interacting protein 2B | −0.7284 | 1.10E−06 |
| 1559439_s_at | C21orf58 | chromosome 21 open reading frame 58 | −0.7256 | 0.0051 |
| 1552960_at | LRRC15 | leucine rich repeat containing 15 | −0.72214 | 0.0049 |
| 204413_at | TRAF2 | TNF receptor-associated factor 2 | −0.69678 | 0.0039 |
| 213888_s_at | TRAF3IP3 | TRAF3 interacting protein 3 | −0.69063 | 0.0043 |
| 1553945_at | GPHB5 | glycoprotein hormone beta 5 | −0.67838 | 0.0003 |
| 221312_at | GLP2R | glucagon-like peptide 2 receptor | −0.67682 | 0.0097 |
| 1554783_s_at | ARHGEF2 | Rho/Rac guanine nucleotide exchange factor (GEF) 2 | −0.67352 | 0.0005 |
| 205567_at | CHST1 | carbohydrate (keratan sulfate Gal-6) sulfotransferase 1 | −0.67335 | 0.0009 |
| 232473_at | PRPF18 | PRP18 pre-mRNA processing factor 18 homolog (*S. cerevisiae*) | −0.66869 | 0.0064 |
| 1565583_at | LOC100291336 | hypothetical protein LOC100291336 | −0.66137 | 0.0086 |
| 243638_at | — | — | −0.65654 | 0.0041 |
| 208608_s_at | SNTB1 | syntrophin, beta 1 (dystrophin-associated protein A1, 59 kDa, basic component 1) | −0.65372 | 0.005 |
| 1556202_at | SRGAP2 | SLIT-ROBO Rho GTPase activating protein 2 | −0.64525 | 0.0034 |
| 206266_at | GPLD1 | glycosylphosphatidylinositol specific phospholipase D1 | −0.64321 | 0.0015 |
| 234659_at | — | — | −0.63414 | 0.007 |
| 204708_at | MAPK4 | mitogen-activated protein kinase 4 | −0.633 | 0.0045 |
| 236604_at | BAHCC1 | BAH domain and coiled-coil containing 1 | −0.63262 | 0.0083 |
| 242129_at | SIN3B | SIN3 homolog B, transcription regulator (yeast) | −0.63025 | 0.0018 |
| 233029_at | OBSCN | obscurin, cytoskeletal calmodulin and titin-interacting RhoGEF | −0.62959 | 0.0049 |
| 203398_s_at | GALNT3 | UDP-N-acetyl-alpha-D-galactosamine:polypeptide | −0.62709 | 0.0016 |

TABLE 2-continued

| Cluster A gene list: Genes up-regulated by HSV and down-regulated by HSV + ATA | | | | |
|---|---|---|---|---|
| Probe_Set_ID | Gene Symbol | Gene_Title | Estimate of HSV1_ATA_vs_HSV1 | p-Value for Estimate of HSV1_ATA_vs_HSV1 |
| | | N-acetylgalactosaminyltransferase 3 (GalNAc-T3) | | |
| 242701_at | TBRG1 | transforming growth factor beta regulator 1 | −0.62074 | 0.0032 |
| 235083_at | LOC151009 | hypothetical LOC151009 | −0.61926 | 0.004 |
| 206372_at | MYF6 | myogenic factor 6 (herculin) | −0.6146 | 0.0018 |
| 1567611_at | — | — | −0.61369 | 0.0061 |
| 236252_at | — | — | −0.61329 | 0.0041 |
| 206286_s_at | TDGF1 /// TDGF3 | teratocarcinoma-derived growth factor 1 /// teratocarcinoma-derived growth factor 3, pseudogene | −0.61123 | 0.0012 |
| 1563263_at | PLCG2 | Phospholipase C, gamma 2 (phosphatidylinositol-specific) | −0.60753 | 0.0003 |
| 214742_at | AZI1 | 5-azacytidine induced 1 | −0.60464 | 0.0089 |
| 244656_at | RASL10B | RAS-like, family 10, member B | −0.6032 | 0.0072 |
| 1555665_at | — | — | −0.59953 | 0.0088 |
| 224291_at | CACNG6 | calcium channel, voltage-dependent, gamma subunit 6 | −0.59548 | 0.0068 |
| 235616_at | TSHZ2 | teashirt zinc finger homeobox 2 | −0.59219 | 0.0037 |
| 237461_at | NLRP7 | NLR family, pyrin domain containing 7 | −0.58969 | 0.0068 |
| 223693_s_at | RADIL | Ras association and DIL domains | −0.58969 | 0.0052 |
| 208454_s_at | PGCP | plasma glutamate carboxypeptidase | −0.58916 | 0.001 |
| 216426_at | TCEB1 | transcription elongation factor B (SIII), polypeptide 1 (15 kDa, elongin C) | −0.58852 | 0.002 |

TABLE 3A

| nNOS, iNOS and eNOS expression reduction in HSV + ATA Samples analyzed by Affymetrix Gen Array; NOS1 = nNOS, NOS2 = iNOS, NOS3 = eNOS | | | | | | | | |
|---|---|---|---|---|---|---|---|---|
| Probe_Set_ID | Pub_ID | Symbol | ATA | HSV | HSV + ATA | p-Val ATA | p-Val HSV | p-Val HSV + ATA |
| 240911_at | AI733341 | NOS1 | 1.02 | 1.71 | 1.5 | 0.872 | 0.009 | 0.024 |
| 207310_s_at | U31466 | NOS1 | 1 | 2.79 | 1.67 | 0.981 | 0.003 | 0.033 |
| AF049656 | — | NOS2 | −1.03 | 2.05 | 1.72 | 0.706 | 0.002 | 0.007 |
| 205581_s_at | NM_000603 | NOS3 | 1.24 | 2.45 | 1.94 | 0.234 | 0.005 | 0.013 |

TABLE 3B

| iNOS expression reduction in HSV + ATA Samples analyzed by SABiosciences (QIAGEN) Jak-Stat RT-PCR Microarray | | | | | | | | |
|---|---|---|---|---|---|---|---|---|
| RT2 Catalog | Pub_ID | Symbol | ATA | HSV | HSV + ATA | p-Val ATA | p-Val HSV | p-Val HSV + ATA |
| 240911_at | AI733341 | NOS1 | 1.02 | 1.71 | 1.5 | 0.872 | 0.009 | 0.024 |

The invention claimed is:

1. A method for producing herpes simplex-1 virus (HSV-1) comprising culturing cells infected with said herpes simplex-1 virus in a cell culture medium that comprises aurintricarboxylic acid and serum, wherein the aurintricarboxylic acid is unfractionated, wherein aurintricarboxylic acid is at a concentration of about 5 μM to about 75 μM, and wherein the cells are 293 or Vero cells.

2. The method of claim 1, wherein said HSV-1 is a wild type HSV-1.

3. The method of claim 1, wherein said HSV-1 is a recombinant HSV-1 .

4. The method of claim 3, wherein said recombinant HSV-1 is HSV-1 d27.1.

5. The method of claim 1, wherein said Vero cells are V27 cells.

6. A method for producing HSV-1 d27.1 comprising:

(a) infecting V27 cells with said HSV-1 d27.1; and (b) culturing said infected V27 cells in a cell culture medium comprising serum, and aurintricarboxylic acid, wherein aurintricarboxylic acid is at a concentration of about 5 μM to about 75 μM, and wherein aurintricarboxylic acid is unfractionated.

7. The method of claim 6, wherein the serum is fetal bovine serum.

8. A cell culture comprising aurintricarboxylic acid, serum and 293 or Vero cells infected with HSV-1, wherein aurintricarboxylic acid is unfractionated, wherein aurintricarboxylic acid is at a concentration of about 5 μM to about 75 μM.

9. The cell culture of claim 8 wherein said Vero cells are V27 cells.

* * * * *

UNITED STATES PATENT AND TRADEMARK OFFICE

CERTIFICATE OF CORRECTION

PATENT NO. : 11,299,715 B2
APPLICATION NO. : 14/758785
DATED : April 12, 2022
INVENTOR(S) : Peter Pechan It is certified that error appears in the above-identified patent and that said Letters Patent is hereby corrected as shown below:

On the Title Page

Item “Inventors”, left hand side column, second line of item (72) please replace “Canbridge, MA (US)” with --Cambridge, MA (US)--; and Item “Assignee”, left hand side column, second line of item (73) please replace “(GB)” with --(US)--.

In the Claims

In Claim 1, Column 40, above TABLE 3A, Line 38 (approx.), please delete “boxylic acid is unfractionated, wherein aurintricarboxylic”; and In Claim 1, Column 40, Lines 63-64, please replace “acid is at a concentration of about 5 μM to about 75 μM, and wherein the cells are 293 or Vero cells” with --boxylic acid is unfractionated, wherein aurintricarboxylic acid is at a concentration of about 5 μM to about 75 μM, and wherein the cells are 293 or Vero cells--.

Signed and Sealed this
Twenty-seventh Day of September, 2022

Katherine Kelly Vidal

Katherine Kelly Vidal
*Director of the United States Patent and Trademark Office*